US007892229B2

(12) United States Patent (10) Patent No.: US 7,892,229 B2
Shadduck et al. (45) Date of Patent: Feb. 22, 2011

(54) MEDICAL INSTRUMENTS AND TECHNIQUES FOR TREATING PULMONARY DISORDERS

(75) Inventors: John H. Shadduck, Menlo Park, CA (US); Michael Hoey, Shoreview, MN (US)

(73) Assignee: Tsunami MedTech, LLC, Menlo Park, CA (US)

( * ) Notice: Subject to any disclaimer, the term of this patent is extended or adjusted under 35 U.S.C. 154(b) by 1390 days.

(21) Appl. No.: 11/158,930

(22) Filed: Jun. 22, 2005

(65) Prior Publication Data

US 2008/0132826 A1 Jun. 5, 2008

Related U.S. Application Data

(63) Continuation-in-part of application No. 10/681,625, filed on Oct. 7, 2003, now Pat. No. 7,674,259, and a continuation-in-part of application No. 10/346,877, filed on Jan. 18, 2003, now Pat. No. 6,911,028.

(60) Provisional application No. 60/615,900, filed on Oct. 5, 2004.

(51) Int. Cl.
 *A61B 18/18* (2006.01)
(52) U.S. Cl. .......................................... 606/41; 606/27
(58) Field of Classification Search ................... 606/24, 606/27–32, 38–41, 45–50; 607/101–105
 See application file for complete search history.

(56) References Cited

U.S. PATENT DOCUMENTS 3,880,168 A 4/1975 Berman (Continued)

FOREIGN PATENT DOCUMENTS

WO WO 00/11927 3/2000

(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

(Continued)

*Primary Examiner*—Linda C Dvorak
*Assistant Examiner*—Amanda Scott
(74) *Attorney, Agent, or Firm*—Levine Bagade Han LLP

(57) ABSTRACT

A surgical instrument for delivering energy to lung tissue, for example to cause lung volume reduction. In one embodiment, an elongated catheter has a handle portion that includes an interior chamber that is supplied with a biocompatible liquid media under pressure. An energy source delivers energy to the media to cause a liquid-to-vapor phase change within the interior chamber and ejects a flow of vapor media from the working end of the catheter. The delivery of energy and the flow of vapor are controlled by a computer controller to cause a selected pressure and selected volume of vapor to propagate to the extremities of the airways. Contemporaneously, the vapor undergoes a vapor-to-liquid phase transition which delivers a large amount of energy to airway tissue. The thermal energy delivered is equivalent to the heat of vaporization of the fluid media, which shrinks and collapses the treated airways. The treated tissue is the maintained in a collapsed state by means of aspiration for a short interval to enhance tissue remodeling. Thereafter, the patient's wound healing response causes fibrosis and further remodeling to cause permanent lung volume reduction.

27 Claims, 16 Drawing Sheets

U.S. PATENT DOCUMENTS

| | | | |
|---|---|---|---|
| 4,682,596 A * | 7/1987 | Bales et al. .................. 606/39 |
| 4,773,410 A | 9/1988 | Blackmer et al. |
| 4,793,352 A | 12/1988 | Eichenlaub |
| 4,915,113 A | 4/1990 | Holman |
| 4,950,266 A | 8/1990 | Sinofsky |
| 5,006,119 A | 4/1991 | Acker et al. |
| 5,011,566 A | 4/1991 | Hoffman |
| 5,084,043 A | 1/1992 | Hertzmann et al. |
| 5,112,328 A | 5/1992 | Taboada et al. |
| 5,122,138 A * | 6/1992 | Manwaring .................. 606/46 |
| 5,158,536 A | 10/1992 | Sekins et al. |
| 5,263,951 A | 11/1993 | Spears et al. |
| 5,298,298 A | 3/1994 | Hoffman |
| 5,318,014 A | 6/1994 | Carter |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,424,620 A | 6/1995 | Cheon et al. |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,591,157 A | 1/1997 | Hennings et al. |
| 5,620,440 A | 4/1997 | Heckele et al. |
| 5,669,907 A | 9/1997 | Platt et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A * | 12/1997 | Eggers et al. ............... 604/114 |
| 5,697,882 A | 12/1997 | Eggers et al. |
| 5,697,909 A | 12/1997 | Eggers et al. |
| 5,700,262 A | 12/1997 | Acosta et al. |
| 5,707,352 A * | 1/1998 | Sekins et al. ............... 604/509 |
| 5,735,811 A | 4/1998 | Brisken |
| 5,741,248 A * | 4/1998 | Stern et al. .................. 606/21 |
| 5,752,965 A | 5/1998 | Francis et al. |
| 5,755,753 A | 5/1998 | Knowlton |
| 5,782,914 A | 7/1998 | Schankereli |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,843,019 A | 12/1998 | Eggers et al. |
| 5,843,073 A | 12/1998 | Sinofsky |
| 5,891,095 A | 4/1999 | Eggers et al. |
| 5,891,134 A * | 4/1999 | Goble et al. .................. 606/27 |
| 5,913,856 A | 6/1999 | Chia et al. |
| 5,944,715 A | 8/1999 | Goble et al. |
| 5,957,919 A | 9/1999 | Laufer |
| 5,964,752 A | 10/1999 | Stone |
| 5,986,662 A | 11/1999 | Argiro et al. |
| 5,989,445 A | 11/1999 | Wise et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,059,011 A | 5/2000 | Giolo |
| 6,066,134 A | 5/2000 | Eggers et al. |
| 6,083,255 A | 7/2000 | Laufer et al. |
| 6,099,251 A | 8/2000 | LaFleur |
| 6,113,722 A | 9/2000 | Hoffman et al. |
| 6,130,671 A | 10/2000 | Argiro |
| 6,139,571 A | 10/2000 | Fuller et al. |
| 6,149,620 A | 11/2000 | Eggers et al. |
| 6,159,194 A | 12/2000 | Eggers et al. |
| 6,162,232 A * | 12/2000 | Shadduck .................. 606/131 |
| 6,168,594 B1 | 1/2001 | LaFontaine et al. |
| 6,190,381 B1 | 2/2001 | Olsen et al. |
| 6,194,066 B1 | 2/2001 | Hoffman |
| 6,200,333 B1 | 3/2001 | Laufer |
| 6,210,404 B1 | 4/2001 | Shadduck |
| 6,219,059 B1 | 4/2001 | Argiro |
| 6,224,592 B1 | 5/2001 | Eggers et al. |
| 6,235,020 B1 | 5/2001 | Cheng et al. |
| 6,261,286 B1 | 7/2001 | Goble et al. |
| 6,264,650 B1 | 7/2001 | Hovda et al. |
| 6,264,651 B1 | 7/2001 | Underwood et al. |
| 6,277,112 B1 | 8/2001 | Underwood et al. |
| 6,283,961 B1 | 9/2001 | Underwood et al. |
| 6,283,989 B1 | 9/2001 | Laufer et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,327,505 B1 | 12/2001 | Medhkour et al. |
| 6,355,032 B1 | 3/2002 | Hovda et al. |
| 6,391,025 B1 | 5/2002 | Weinstein et al. |
| 6,394,949 B1 | 5/2002 | Crowley et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,695 B2 | 10/2002 | Hovda et al. |
| 6,468,274 B1 | 10/2002 | Alleyne et al. |
| 6,468,313 B1 | 10/2002 | Claeson et al. |
| 6,482,201 B1 | 11/2002 | Olsen et al. |
| 6,488,673 B1 * | 12/2002 | Laufer et al. ................ 604/516 |
| 6,493,589 B1 | 12/2002 | Medhkour et al. |
| 6,508,816 B2 | 1/2003 | Shadduck |
| 6,527,761 B1 | 3/2003 | Soltesz et al. |
| 6,540,741 B1 | 4/2003 | Underwood et al. |
| 6,575,968 B1 | 6/2003 | Eggers et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,620,155 B2 | 9/2003 | Underwood et al. |
| 6,632,193 B1 | 10/2003 | Davison et al. |
| 6,632,220 B1 | 10/2003 | Eggers et al. |
| 6,634,363 B1 * | 10/2003 | Laufer et al. ................ 128/898 |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,694 B2 | 12/2003 | Shadduck |
| 6,679,264 B1 | 1/2004 | Deem et al. |
| 6,679,879 B2 | 1/2004 | Shadduck |
| 6,682,520 B2 | 1/2004 | Ingenito |
| 6,692,494 B1 | 2/2004 | Cooper et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,726,684 B1 | 4/2004 | Woloszko et al. |
| 6,746,447 B2 | 6/2004 | Davison et al. |
| 6,755,794 B2 | 6/2004 | Soukup |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,776,765 B2 | 8/2004 | Soukup et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,860,847 B2 | 3/2005 | Alferness et al. |
| 6,901,927 B2 | 6/2005 | Deem et al. |

| | | |
|---|---|---|
| 6,904,909 B2 | 6/2005 | Andreas et al. |
| 6,907,881 B2 | 6/2005 | Suki et al. |
| 6,911,028 B2 | 6/2005 | Shadduck |
| 6,929,640 B1 | 8/2005 | Underwood et al. |
| 6,986,769 B2 | 1/2006 | Nelson et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,192,400 B2 | 3/2007 | Campbell et al. |
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian et al. |
| 7,549,987 B2 | 6/2009 | Shadduck |
| 7,674,259 B2 | 3/2010 | Shadduck |
| 2001/0020167 A1 | 9/2001 | Woloszko et al. |
| 2001/0029370 A1 | 10/2001 | Hovda et al. |
| 2001/0037106 A1 | 11/2001 | Shadduck |
| 2002/0077516 A1 | 6/2002 | Flanigan |
| 2002/0082667 A1* | 6/2002 | Shadduck ............ 607/96 |
| 2002/0095152 A1 | 7/2002 | Ciarrocca et al. |
| 2002/0111386 A1 | 8/2002 | Sekins et al. |
| 2002/0177846 A1* | 11/2002 | Mulier et al. ............ 606/27 |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0099279 A1 | 5/2003 | Venkatasubramanian et al. |
| 2003/0109869 A1 | 6/2003 | Shadduck |
| 2003/0130655 A1 | 7/2003 | Woloszko et al. |
| 2003/0130738 A1 | 7/2003 | Hovda et al. |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212395 A1 | 11/2003 | Woloszko et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068306 A1 | 4/2004 | Shadduck |
| 2004/0087937 A1 | 5/2004 | Eggers et al. |
| 2004/0116922 A1 | 6/2004 | Hovda et al. |
| 2004/0199226 A1 | 10/2004 | Shadduck |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0119650 A1 | 6/2005 | Sanders et al. |
| 2005/0166925 A1 | 8/2005 | Wilson et al. |
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2006/0004400 A1 | 1/2006 | McGurk et al. |
| 2006/0047291 A1 | 3/2006 | Barry |
| 2006/0100619 A1 | 5/2006 | McClurken et al. |
| 2006/0130830 A1 | 6/2006 | Barry |
| 2006/0135955 A1 | 6/2006 | Shadduck |
| 2006/0161233 A1 | 7/2006 | Barry et al. |
| 2006/0200076 A1 | 9/2006 | Gonzalez et al. |
| 2006/0224154 A1 | 10/2006 | Shadduck et al. |
| 2007/0036417 A1 | 2/2007 | Argiro et al. |
| 2007/0091087 A1 | 4/2007 | Zuiderveld |
| 2008/0033493 A1 | 2/2008 | Deckman et al. |
| 2008/0103566 A1 | 5/2008 | Mehier |
| 2008/0110457 A1 | 5/2008 | Barry et al. |
| 2008/0114297 A1 | 5/2008 | Barry et al. |
| 2009/0105702 A1 | 4/2009 | Shadduck |
| 2009/0105703 A1 | 4/2009 | Shadduck |
| 2009/0149846 A1 | 6/2009 | Hoey et al. |
| 2009/0216220 A1 | 8/2009 | Hoey et al. |
| 2009/0312753 A1 | 12/2009 | Shadduck |
| 2010/0160905 A1 | 6/2010 | Shadduck |

FOREIGN PATENT DOCUMENTS

| | | |
|---|---|---|
| WO | WO 00/29055 | 5/2000 |
| WO | WO 02/69821 | 9/2002 |
| WO | WO 03/070302 | 8/2003 |
| WO | WO 03/86498 | 10/2003 |
| WO | WO 2005/025635 | 3/2005 |
| WO | WO 2005/102175 | 11/2005 |
| WO | WO 2006/003665 | 1/2006 |
| WO | WO 2009/009398 | 1/2009 |

OTHER PUBLICATIONS

Fishman et al., "A randomized trial comparing lung-volume-reduction surgery with medical therapy for severe emphysema," *N. Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp. 159-164, Aug. 1986.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3, pp. 781-787, Mar. 2001.

Moulding et al., "Preliminary studies for achieving transcervical oviduct occlusion by hot water or low-pressure steam," *Advancesin Planned Parenthood*, vol. 12, No. 2; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.

U.S. Appl. No. 09/181,906, filed Oct. 28, 1998, in the name of Shadduck, Non-Final Rejection mailed Mar. 15, 2000.

U.S. Appl. No. 09/181,906, filed Oct. 28, 1998, in the name of Shadduck, Notice of Allowance mailed Sep. 26, 2000.

U.S. Appl. No. 09/782,649, filed Feb. 12, 2001, in the name of Shadduck, Notice of Allowance mailed Sep. 9, 2002.

U.S. Appl. No. 10/017,582, filed Dec. 7, 2001, in the name of Shadduck, Non-Final Rejection mailed Dec. 10, 2002.

U.S. Appl. No. 10/017,582, filed Dec. 7, 2001, in the name of Shadduck, Non-Final Rejection mailed Jul. 17, 2003.

U.S. Appl. No. 10/346,877, filed Jan. 18, 2003, in the name of Shadduck, Non-Final Rejection mailed Sep. 30, 2004.

U.S. Appl. No. 10/346,877, filed Jan. 18, 2003, in the name of Shadduck, Examiner's Amendment mailed Mar. 7, 2005.

U.S. Appl. No. 10/346,877, filed Jan. 18, 2003, in the name of Shadduck, Notice of Allowance mailed Mar. 7, 2005.

U.S. Appl. No. 11/244,329, filed Jan. 18, 2003, in the name of Shadduck, Non-Final Rejection mailed Jun. 19, 2009.

U.S. Appl. No. 10/681,625, filed Oct. 7, 2003, in the name of Shadduck, Non-Final Rejection mailed Mar. 13, 2009.

U.S. Appl. No. 10/681,625, filed Oct. 7, 2003, in the name of Shadduck, Non-Final Rejection mailed Aug. 15, 2007.

U.S. Appl. No. 10/681,625, filed Oct. 7, 2003, in the name of Shadduck, Final Rejection mailed Jun. 3, 2008.

U.S. Appl. No. 12/465,927, filed May 14, 2009, in the name of Shadduck, entitled "Thermotherapy device".

U.S. Appl. No. 09/580,767, filed May 30, 2000 in the name of Shadduck, entitled "Microjoule electrical discharge catheter for thrombolysis in stroke patients".

U.S. Appl. No. 09/557,931, filed Apr. 22, 2000 in the name of Shadduck, entitled "Ionothermal delivery system and technique for medical procedures".

U.S. Appl. No. 09/281,493, filed Mar. 30, 1999 in the name of Shadduck, entitled "Ionothermal system and technique for dermal treatments".

Topaz, et at, "Acute Results, Complications, and Effect of Lesion Characteristics on Outcome With the Solid-State, Pulsed Wave, Mid-Infrared Laser Angioplasty System", *Lasers in Surg. & Med.*, vol. 22, pp. 228-239, 1998.

U.S. Appl. No. 10/681,625 filed Oct. 7, 2003, in the name of Shadduck, Notice of Allowance mailed Dec. 30, 2009.

U.S. Appl. No. 10/830,372 filed Apr. 22, 2004, in the name of Shadduck, Final Office Action mailed May 21, 2008.

U.S. Appl. No. 10/830,372 filed Apr. 22, 2004, in the name of Shadduck, Non-Final Office Action mailed Aug. 15, 2007.

U.S. Appl. No. 10/830,372 filed Apr. 22, 2004, in the name of Shadduck, Notice of Allowance mailed Apr. 7, 2009.

U.S. Appl. No. 11/244,329 filed Oct. 5, 2005, in the name of Shadduck, Non-Final Office Action mailed Mar. 22, 2010.

U.S. Appl. No. 11/329,381 filed Jan. 10, 2006, in the name of Shadduck, Final Office Action mailed Jul 14, 2010.

U.S. Appl. No. 11/329,381 filed Jan. 10, 2006, in the name of Shadduck, Non-Final Office Action mailed Dec. 9, 2009.

\* cited by examiner

MEDICAL INSTRUMENTS AND TECHNIQUES FOR TREATING PULMONARY DISORDERS

CROSS-REFERENCE TO RELATED APPLICATIONS

This application claims benefit of U.S. Provisional Patent Application No. 60/615,900 filed Oct. 5, 2004 titled Medical Instruments and Techniques for Thermally-Mediated Procedures. This application is also a continuation-in-part of U.S. patent application Ser. No. 10/346,877 filed Jan. 18, 2003 now U.S. Pat. No. 6,911,028 titled Medical Instrument Working End and Method for Endoluminal Treatment, the entire contents of which is incorporated herein by this reference and should be considered a part of this specification. This application is also a continuation-in-part application of U.S. application Ser. No. 10/681,625, filed Oct. 7, 2003 now U.S. Pat. No. 7,674,259.

BACKGROUND OF THE INVENTION

1. Field of the Invention

The present invention relates generally to methods and systems for applying energy to tissue, and more particularly to methods and systems for injecting vapor media into an airway and causing a vapor-to-liquid phase state change to thereby apply thermal energy equivalent to the heat of vaporization of the vapor media into the lung. The delivery of energy is accomplished with a catheter in a minimally invasive procedure to shrink, seal and ablate a targeted region to reduce the effective volume of a patient's lung.

2. Description of the Related Art

Emphysema is a debilitating illness brought about by the destruction of lung tissue. The disorder affects up to 10% of the population over 50 years old. Emphysema is most commonly caused by cigarette smoking and, in some cases, by a genetic deficiency. The condition is characterized by abnormalities of the alveoli, which are the microscopic air sacs in the lung where gas exchange takes place. Destruction of these air sacs makes it difficult for the body to obtain oxygen and to get rid of carbon dioxide.

In emphysema, there is a progressive decline in respiratory function due to a loss of lung elastic recoil with a decrease of expiratory flow rates. The damage to the microscopic air sacs of the lung results in air-trapping and hyperinflation of the lungs. As the damaged air sacs enlarge, they push on the diaphragm making it more difficult to breathe. The enlarged air sacs also exert compressive forces on undamaged lung tissues, which further reduces gas exchange by the undamaged lung portions. These changes produce the major symptom emphysema patients suffer—dyspnea (shortness of breath) and difficulty of expiration. Current pharmacological treatments for emphysema include bronchodilators to improve airflow. Also, oxygen therapy is used for patients with chronic hypoxemia.

More recently, a surgical procedure called lung volume reduction (LVR) has been developed to alleviate symptoms of advanced chronic obstructive lung disease that results from emphysema. This surgical resection is variably referred to as lung reduction surgery or reduction pneumoplasty in which the most severely emphysematous lung tissue is resected.

The development of LVR was based on the observation that emphysema causes the diseased lung to expand and compress the normally functioning lung tissue. If the diseased lung tissue were removed, it was believed that the additional space in the chest cavity would allow the normal lung tissue to expand and carry on gas exchange. LVR was first introduced in the 1950's but was initially abandoned due to a high operative mortality, primarily due to air leakage. One of the main difficulties of the procedure is suturing the resected lung margin in an airtight manner. Normally there is a vacuum between the ribs and the lungs that helps to make the lungs expand and fill with air when the chest wall expands. If an air leak allows air in the potential space between the ribs and lungs—then the vacuum effect will disappear and the lungs will sag upon chest expansion making it increasingly difficult to inflate the lungs and perform gas exchange.

Currently, there are two principal surgical approaches for LVR—both of which involve removal of diseased lung tissue (typically in the upper lobes) followed by surgical stapling of the remaining lung to close up the incision. One approach is an open surgery in which the surgeon uses a median sternotomy to access the chest cavity for removal of diseased lung tissue. The second approach is a video-assisted thoracic surgery in which endoscopic instruments are inserted into the chest cavity through small incisions made on either side of the chest. LVR downsizes the lungs by resecting badly diseased emphysematous tissue that is functionally useless. Surgeons generally remove approximately 20-30% of each lung in a manner that takes advantage of the heterogeneity of emphysema in which the lesions are usually more severe at the apices and less severe at the lung bases. During the course of surgery, one lung is continually ventilated while the lumen of the contralateral lung is clamped. Subsequently, normal areas of the lung deflate as blood flows past the alveoli and resorbs oxygen, while emphysematous portions of the lung with less blood flow and reduced surface area remain inflated and are targeted for resection. The more recent procedures use bovine pericardium or other biocompatible films to buttress a staple line along the resected lung margin to minimize air leaks.

LVR improves function of the lung by restoring pulmonary elastic recoil and correcting over-distention of the thorax and depression of the diaphragm. Thus, the objective of LVR is to provide the patient with improved respiratory mechanics and relief from severe shortness of breath upon exertion. Many patients have reported benefits such as improved airflow, increased functional lung capacity and an improved quality of life. As in any major thoracic procedure, there are many risks, including fever, wound infections, wound hematomas, post-operative fatigue and tachycardia. The recuperation period following LVR varies from person to person, but most patients remain in the hospital for two weeks following surgery. The patient then must endure a regime of physical therapy and rehabilitation for several additional months. Further, the duration of the improvement in lung function following resection is not yet completely known—but there is a suggestion that lung function begins to decline two years after LVR. Despite optimistic reports, the morbidity, mortality and financial costs associated with LVR appear to be high, with some studies indicating mortality rates ranging from 4 to 17%.

SUMMARY OF THE INVENTION

In general, a method corresponding to the invention comprises causing a vapor-to-liquid phase state change in a selected media in targeted airways of a patient's lung thereby applying thermal energy substantially equal to the heat of vaporization of the lung. Endothelial-lined structures of the body, such as airways, have substantially collagen cores. Intermolecular cross-links provide collagen connective tissue with unique physical properties such as high tensile strength and substantial elasticity. A well-recognized property of collagen relates to the shrinkage of collagen fibers when elevated in temperature to the range 60° to 80° C. Temperature elevation ruptures the collagen ultrastructural stabilizing cross-links, and results in immediate contraction in the fibers to about one-third of their original longitudinal dimension. Thus, the method of the invention includes delivering thermal energy within the sufficient to collapse and shrink targeted portions of a bronchial tree.

A preferred method delivers large amounts of energy to lung tissue by a vapor-to-liquid phase transition or "internal energy" release from a biocompatible vapor such as saline. FIGS. 1A and 1B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy—that can be released to apply energy to body structure.

It has been found that the controlled application of internal energies in an introduced media-tissue interaction solves many of the vexing problems associated with energy-tissue interactions in conventional Rf, laser, microwave and ultrasound modalities. The apparatus of the invention provides a fluid-carrying chamber in the interior of the device or working end. A source provides liquid media to the interior chamber wherein energy is applied to instantly vaporize the media. In the process of the liquid-to-vapor phase transition of a saline media in the interior of the working end, large amounts of energy are added to overcome the cohesive forces between molecules in the liquid, and an additional amount of energy is requires to expand the liquid 1000+ percent (PΔD) into a resulting vapor phase (see FIG. 1A). Conversely, in the vapor-to-liquid transition, such energy will be released at the phase transitions at the targeted tissue interface. That is, the heat of vaporization is released in tissue when the media transitioning from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy within a targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media within an interior chamber of an instrument's working end. The initial, ascendant energy-media interaction delivers energy sufficient to achieve the heat of vaporization of a selected liquid media such as saline within an interior of the instrument body. This aspect of the technology requires an inventive energy source and controller—since energy application from the source to the selected media (Rf, laser, microwave, ultrasound, inductive heating, etc.) must be modulated between very large energy densities to initially surpass the latent heat of vaporization of the media within milliseconds, and possible subsequent lesser energy densities for maintaining the media in its vapor phase. Additionally, the energy delivery system is coupled to a pressure control system for replenishing the selected liquid phase media at the required rate—and optionally for controlling propagation velocity of the vapor phase media from the working end surface of the instrument. In use, the method of the invention comprises the controlled deposition of a large amount of energy—the heat of vaporization (sometimes referred to as release of heat of condensation) as in FIG. 1A—when the vapor-to-liquid phase transition is controlled at the vapor media-tissue interface. The vapor-to-liquid phase transition deposits about 580 cal/gram within the targeted tissue site to perform the thermal ablation.

In general, the system of the invention is adapted to provide least invasive methods for lung volume reduction that are accomplished by using thermal energy to treat and shrink targeted regions of a the bronchial. In one embodiment, an elongated catheter is configured for introduction in a targeted airway. The handle portion of the catheter includes an interior chamber that is supplied with a biocompatible liquid under pressure. An energy source is coupled to the interior chamber to cause a liquid-to-vapor phase change in the biocompatible liquid, which contemporaneously ejects a flow of vapor from the working end of the catheter. The flow of vapor is controlled by a controller to cause a selected pressure and selected volume of vapor to propagate to alveoli. The vapor flow instantly undergoes a vapor-to-liquid phase change to thereby applying energy to the airway tissue. The thermal energy delivered is equivalent to the heat of vaporization of the fluid media, which shrinks and collapses the treated airways that are not supported by substantial cartilage. The treated tissue is maintained in a collapsed state by means of aspiration for a short interval to enhance tissue remodeling. Thereafter, the patient's wound healing response will cause fibrosis and further remodeling of the treated airway tissue to cause lung volume reduction.

The invention provides a method for LVR that can eliminate the complications of open surgery, endoscopic surgery or various bronchial plugs.

The invention provides a method for LVR that does not require transection of the exterior lung wall thus eliminating the serious complications of air leakage into the chest cavity.

The invention provides a method for LVR that can greatly reduce the patient's recuperative period and hospital stay.

The invention provides a method for LVR that can be repeated over a patient's lifetime.

The invention provides a method for LVR that will allow for greatly reduced costs when compared to open or endoscopic LVR procedures.

Additional advantages of the invention will be apparent from the following description, the accompanying drawings and the appended claims.

DETAILED DESCRIPTION OF THE INVENTION

Figure 1A:
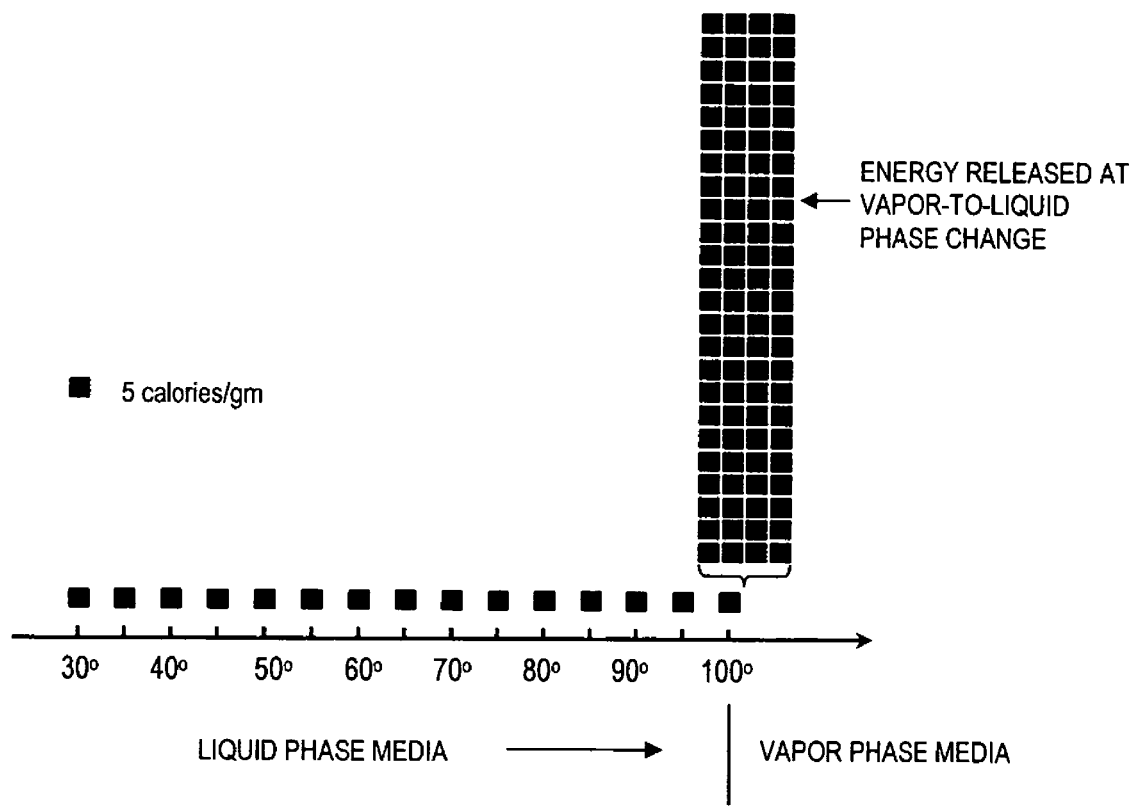
FIG. 1A is a graphical depiction of the quantity of energy needed to achieve the heat of vaporization of water.
Figure 1B:
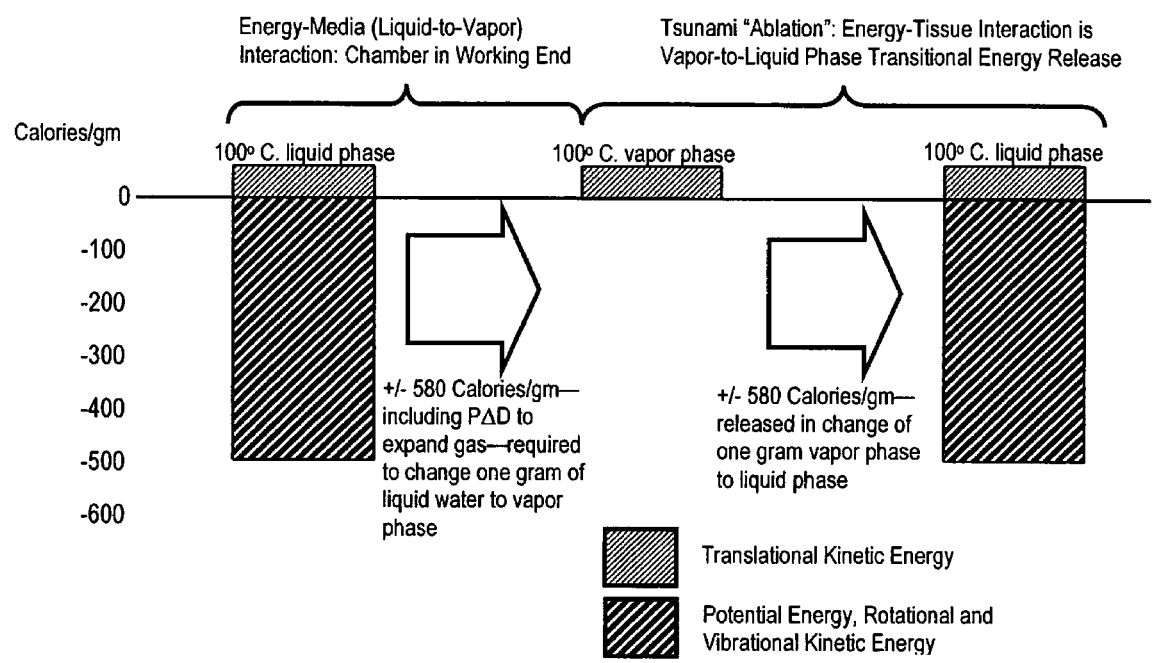
FIG. 1B is a diagram of phase change energy release that underlies one method of the invention.
Figure 2A:
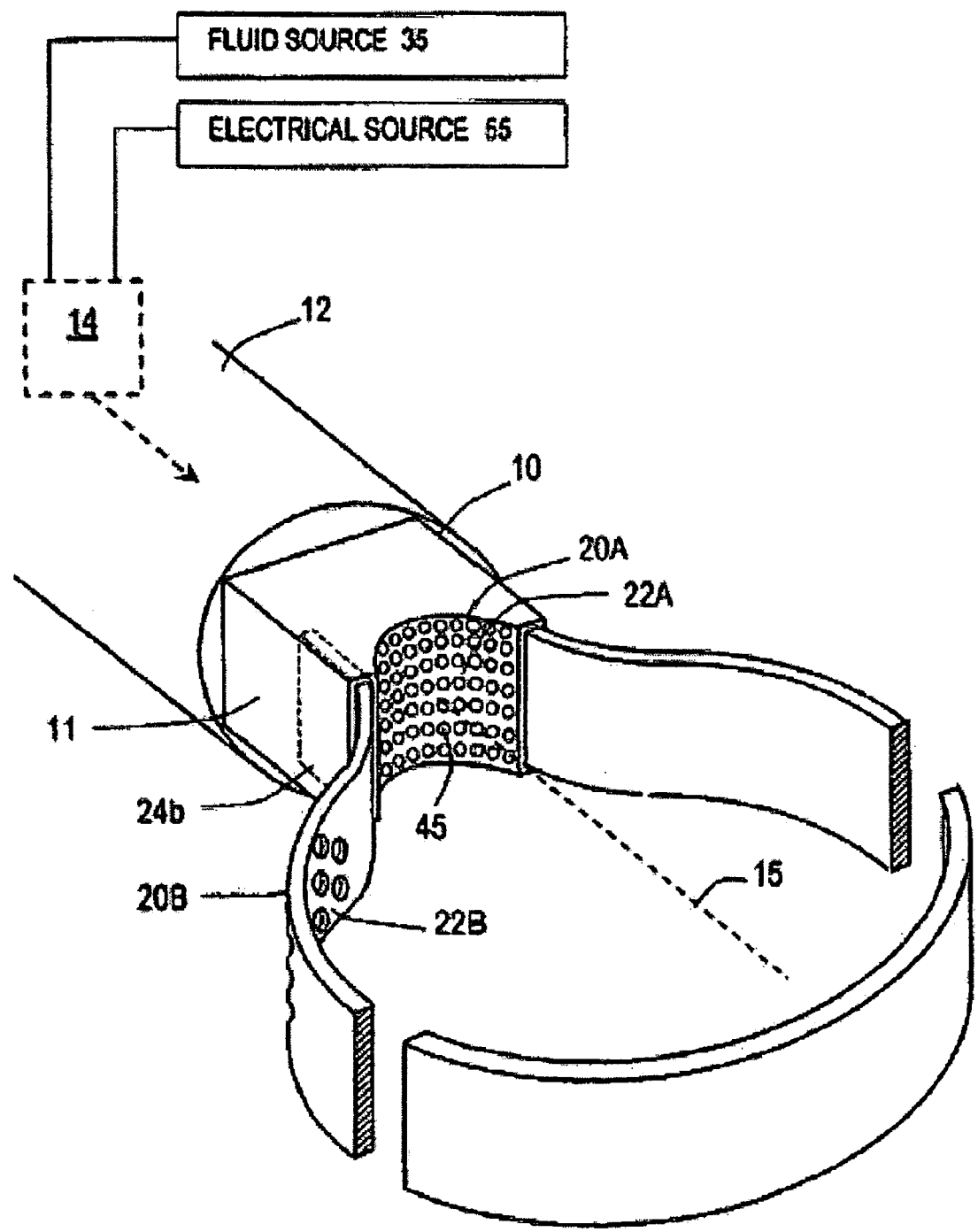
FIG. 2A is a perspective view of the working end of an exemplary Type "A" probe of the present invention with an openable-closeable tissue engaging structure in a first open position.
Figure 2B:
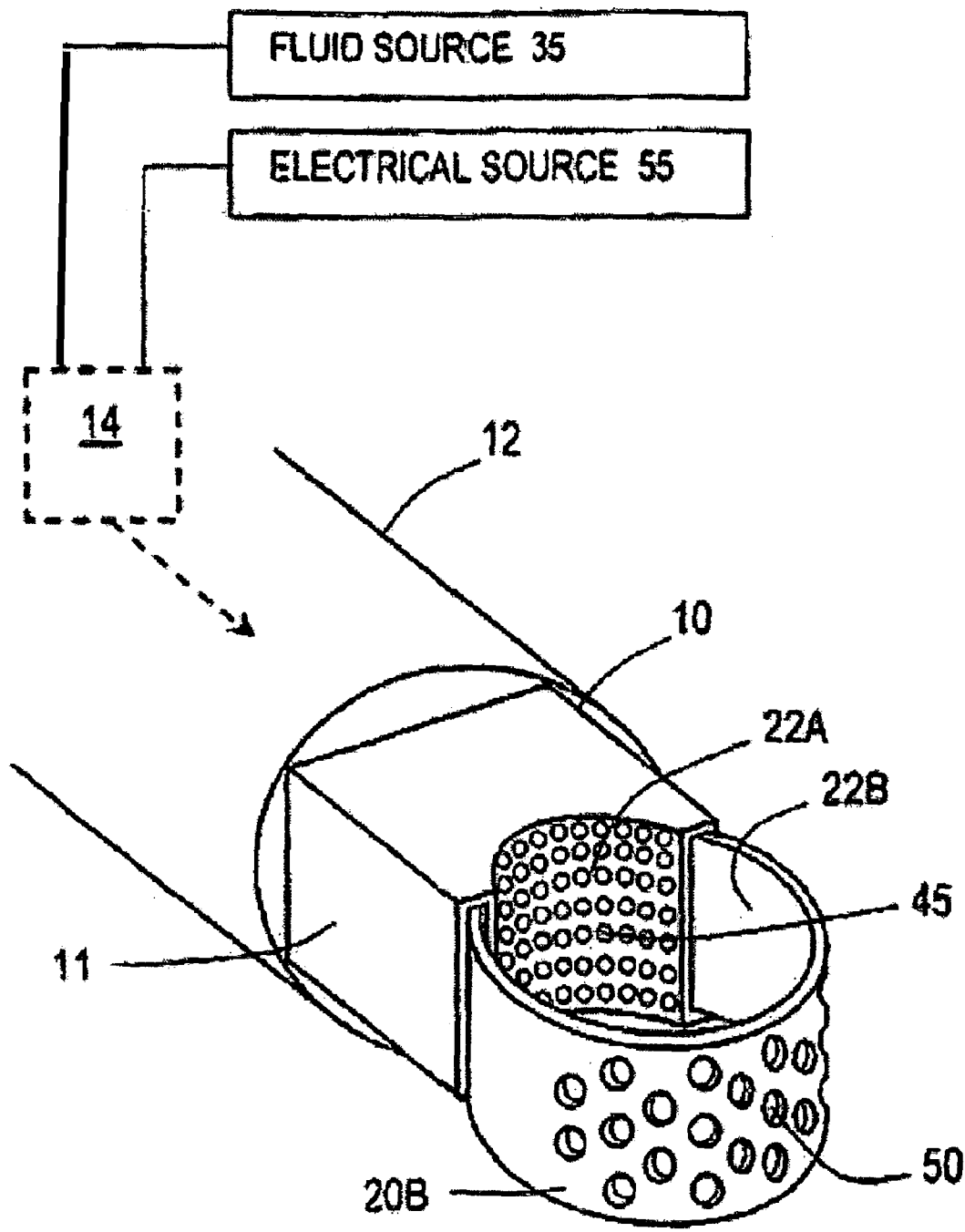
FIG. 2B is a perspective view similar to FIG. 2A probe of the present invention in a second closed position.
Figure 3:
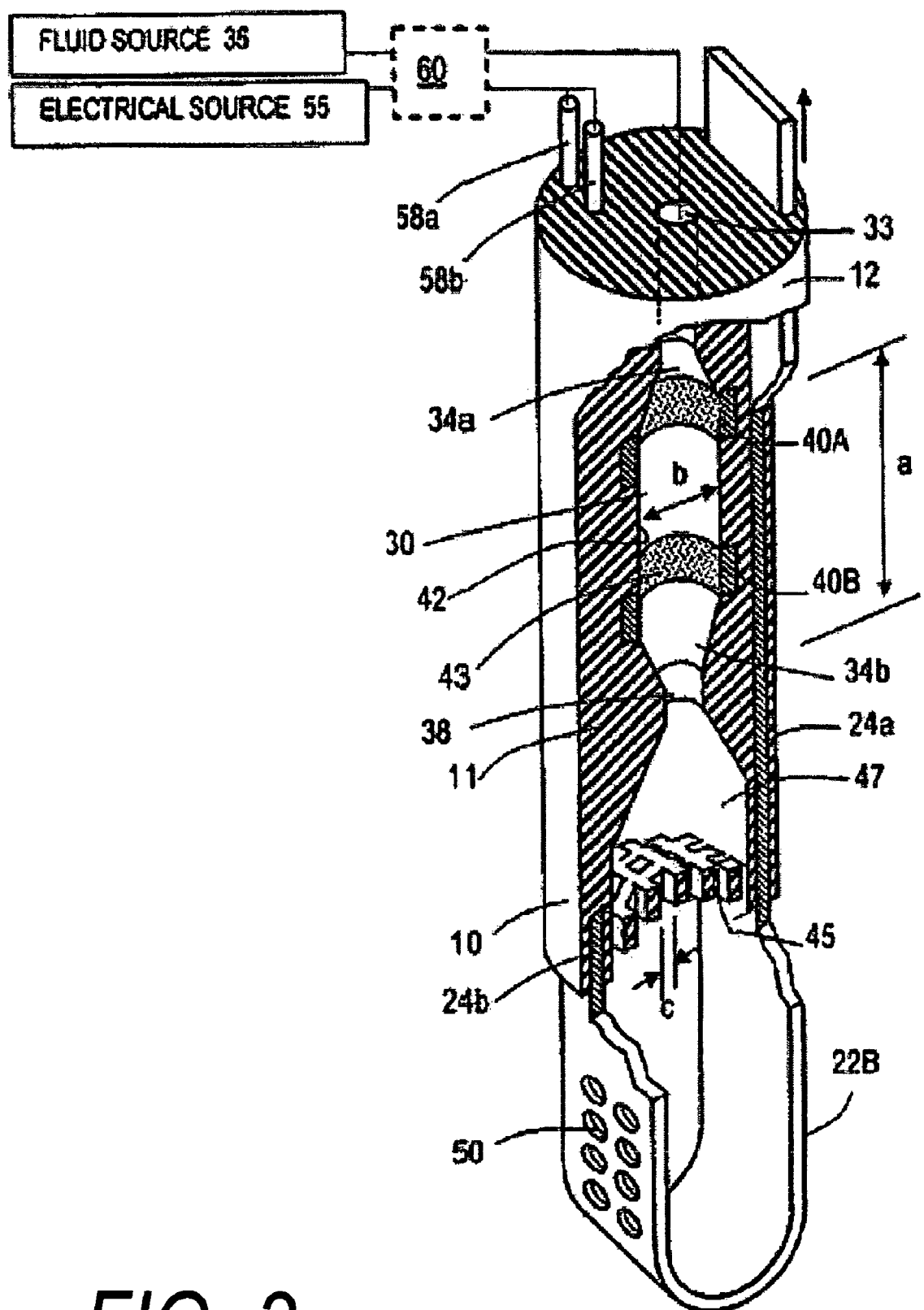
FIG. 3 is a cut-away view of the working end of FIGS. 2A-2B.

1. Type "A" Thermotherapy Instrument. Referring to FIGS. 2A, 2B and 3, the working end 10 of a Type "A" system 5 of the present invention is shown that is adapted for endoscopic procedures in which a tissue volume T targeted for treatment (a thermoplasty) can be captured by a loop structure. The working end 10 comprises a body 11 of insulator material (see FIG. 3) coupled to the distal end of introducer member 12 extending along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm to 5 mm) and in this embodiment is coupled to an elongate flexible introducer member 12 to cooperate with a working channel in an endoscope. Alternatively, the working end 10 may be coupled to a rigid shaft member having a suitable 1 mm to 5 mm or larger diameter to cooperate with a trocar sleeve for use in endoscopic or microsurgical procedures. A proximal handle portion 14 of the instrument indicated by the block diagram of FIG. 2A carries the various actuator mechanisms known in the art for actuating components of the instrument.

In FIGS. 2A, 2B and 3, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises a non-moving component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 3). The other end 24b of the loop structure 22B is fixed in body 11. While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 2A illustrates the first and second tissue-engaging surfaces 20A and 20B in a first spaced apart or open position. FIG. 2B shows the first and second surfaces 20A and 20B moved toward a second closed position.

Now turning to the fluid-to-gas energy delivery means of the invention, referring to FIG. 3, it can be seen that the insulated or non-conductive body 11 of working end 10 carries an interior chamber indicated at 30 communicating with lumen 33 that are together adapted for delivery and transient confinement of a fluid media M that flows into chamber 30. The chamber 30 communicates via lumen 33 with a fluid media source 35 that may be remote from the device, or a fluid reservoir (coupled to a remote pressure source) carried within introducer 12 or carried within a handle portion 14. The term fluid or flowable media source 35 is defined to include a positive pressure inflow system which preferably is any suitable high pressure pump means known in the art. The fluid delivery lumen 33 transitions to chamber 30 at proximal end portion 34a thereof. The distal end portion 34b of chamber 30 has a reduced cross-section that functions to direct vapor media through a small outlet or nozzle indicated at 38.

Of particular interest, still referring to FIG. 3, paired spaced apart electrode elements 40A and 40B are exposed in surface 42 of interior fluid confinement chamber 30. In this exemplary embodiment, the electrode elements 40A and 40B comprise circumferential exposed surfaces of a conductive material positioned at opposing proximal and distal ends of interior chamber 30, but other arrangements are possible. The invention can utilize any suitable configuration of spaced apart electrodes (e.g., such as concentric electrode surfaces, intertwined helical electrode surfaces, adjustable spaced apart surfaces, or porous electrodes) about at least one confinement chamber 30 or lumen portion of the system. Alternatively, each electrode can comprise one or more projecting elements that project into the chamber. The exemplary embodiment of FIG. 3 shows an elongate chamber having an axial dimension indicated at A and diameter or cross-section indicated at B. The axial dimension may range from about 0.1 mm to 20.0 mm and may be singular or plural as described below. The diameter B may range from micron dimensions (e.g., 0.5 μm) for miniaturized instruments to a larger dimension (e.g., 5.0 mm) for larger instruments for causing the thermally induced liquid-to-vapor transformation required to enable the novel phase change energy-tissue interaction of the invention. The electrodes are of any suitable material such as stainless steel, aluminum, nickel titanium, platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 3 further shows that a preferred shape is formed into the tissue-engaging surface 20A to better perform the method of fusing tissue. As can be seen in FIGS. 2B and 3, the first tissue-engaging surface 20A is generally concave so as to be adapted to receive a greater tissue volume in the central portion of surface 20A. The second tissue-engaging surface 20B is flexible and naturally will be concave in the distal or opposite direction when tissue is engaged between surfaces 20A and 20B. This preferred shape structure allows for controllable compression of the thick targeted tissue volumes T centrally exposed to the energy delivery means and helps prevent conductance of thermal effects to collateral tissue regions CT (see FIG. 4) and as will be described in greater detail below.

FIGS. 2A and 3 show that first tissue-engaging surface 20A defines an open structure of at least one aperture or passageway indicated at 45 that allows vapor to pass therethrough. The apertures 45 may have any cross-sectional shape and linear or angular route through surface 20A with a sectional dimension C in this embodiment ranging upwards from micron dimensions (e.g., 0.5 µm) to about 2.0 mm in a large surface 20A. The exemplary embodiment of FIG. 3 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf. apertures 45) and are adapted to generally oppose the first tissue-engaging surface 20A when the surfaces 20A and 20B are in the second closed position, as shown in FIG. 2B.

The electrodes 40A and 40B of working end 10 have opposing polarities and are coupled to Rf generator or electrical source 55. FIG. 3 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 2A). Such a sensor, for example a thermocouple known in the art, can measure temperature at the surface of the captured tissue. The sensor is coupled to controller 60 by a lead (not shown) and can be used to modulate or terminate power delivery as will be described next in the method of the invention.

Figure 4:
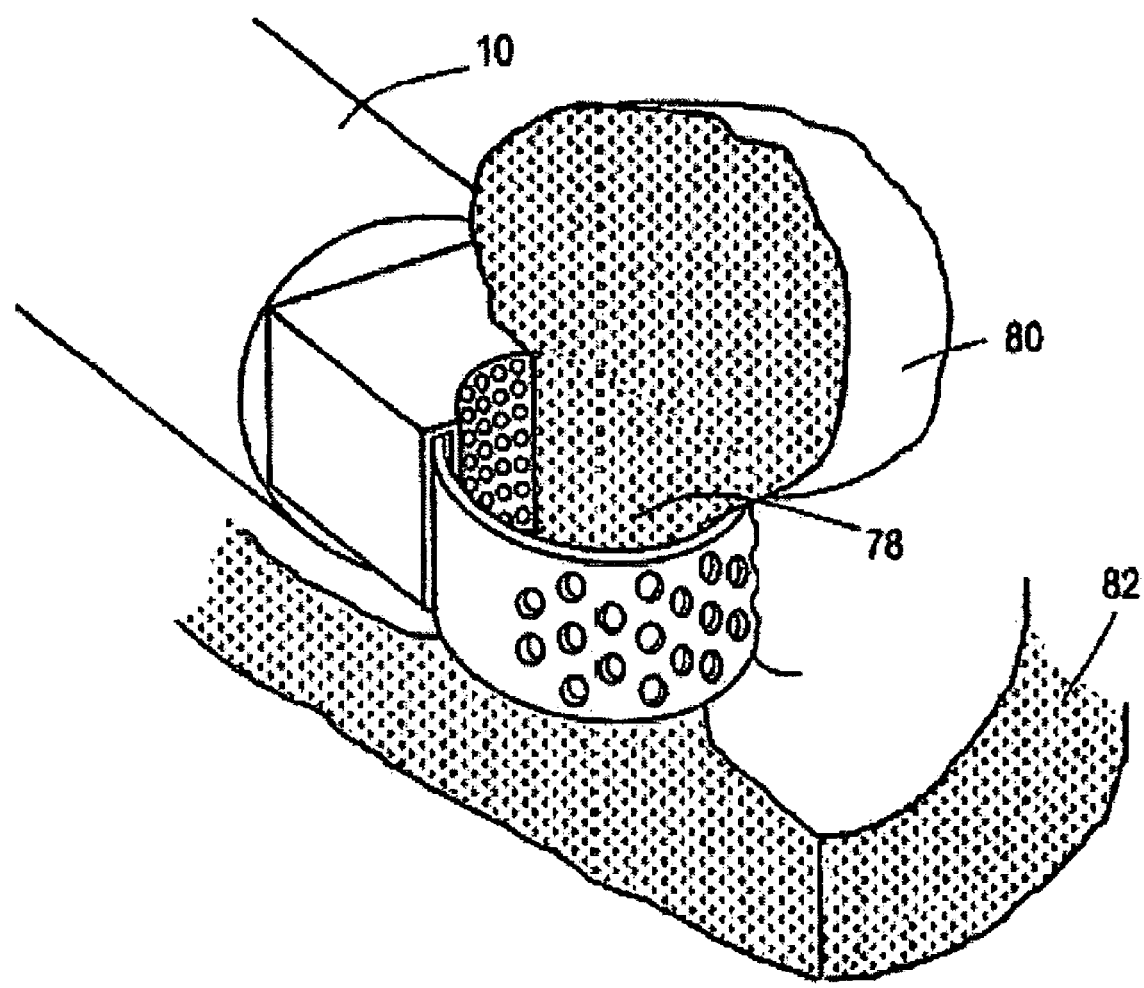
FIG. 4 is a perspective view of the working end of FIG. 3 capturing an exemplary tissue volume.

Operation and use of the working end of FIGS. 2A, 2B and 3 in performing a method of treating tissue can be briefly described as follows, for example in an endoscopic polyp removal procedure. As can be understood from FIG. 4, the working end 10 is carried by an elongate catheter-type member 12 that is introduced through a working channel 70 of an endoscope 72 to a working space. In this case, the tissue T targeted for sealing is a medial portion 78 of a polyp 80 in a colon 82. It can be easily understood that the slidable movement of the loop member 22B can capture the polyp 80 in the device as shown in FIG. 4 after being lassoed. The objective of the tissue treatment is to seal the medial portion of the polyp with the inventive thermotherapy. Thereafter, utilize a separate cutting instrument is used to cut through the sealed portion, and the excised polyp is retrieved for biopsy purposes.

Figure 5:
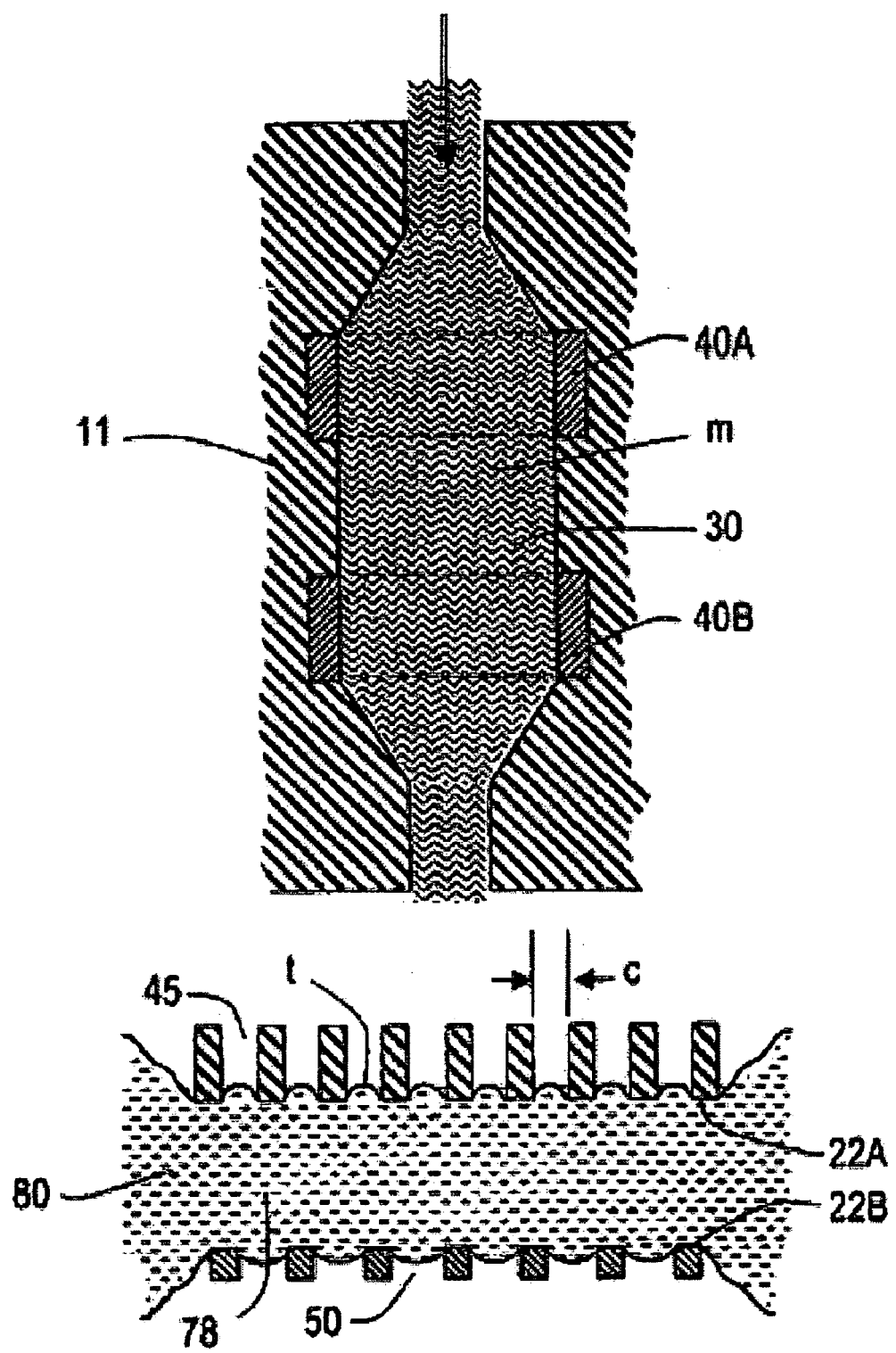
FIGS. 5-6 are sectional schematic views of working end of FIG. 3 depicting, in sequence, the steps of a method of the present invention to seal or weld a targeted tissue volume, FIG. 5 illustrating the pressurized delivery of a liquid media to an interior channel, and FIG. 6 depicting an electrical discharge that causes a liquid-to-gas phase change as well as the ejection of the vapor media into the targeted tissue to thermally seal engaged tissue.
Figure 6:
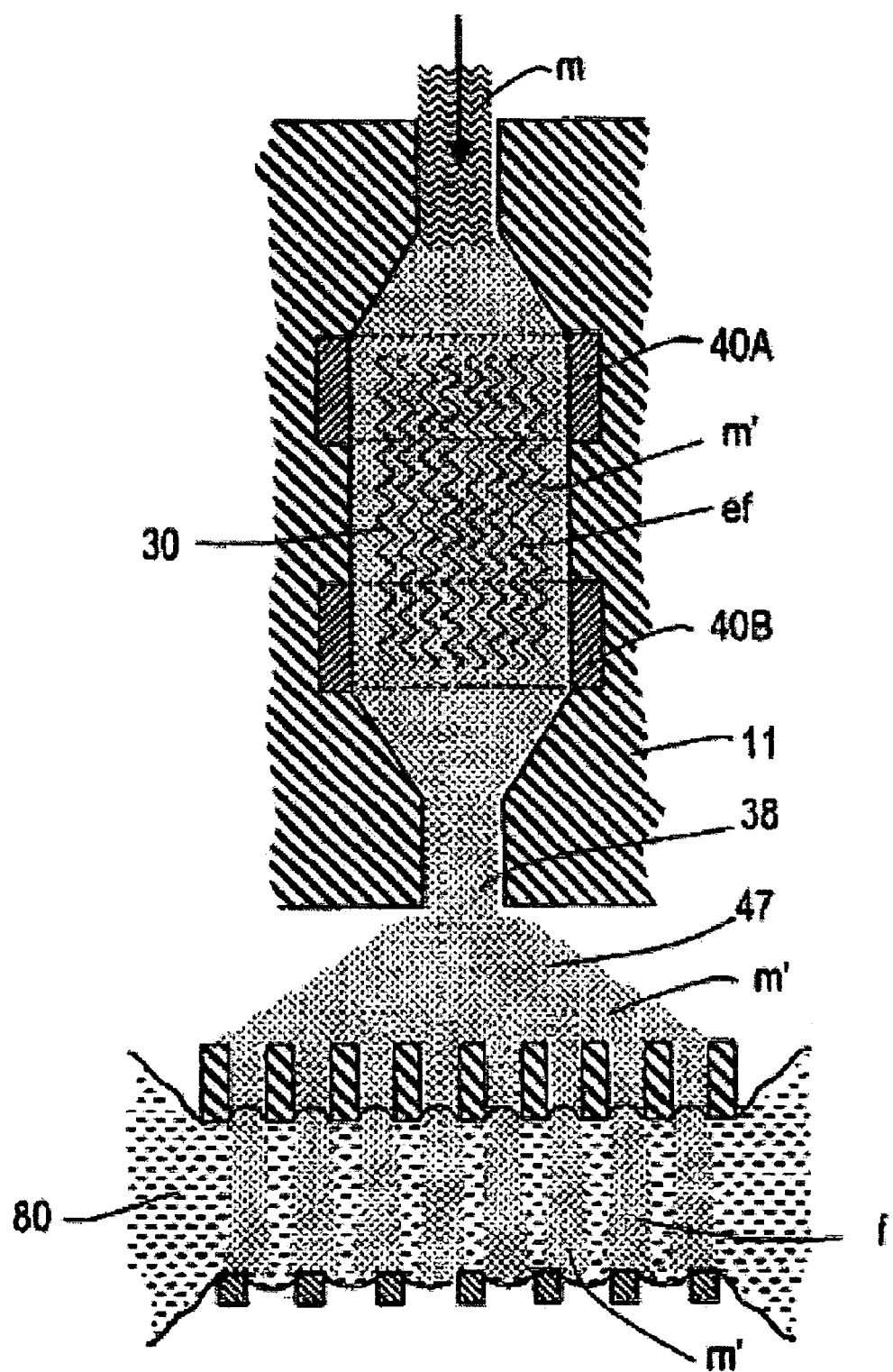

Now turning to FIGS. 5 and 6, two sequential schematic views of the working end engaging tissue T are provided to illustrate the energy-tissue interaction caused by the method of the invention. FIG. 5 depicts an initial step of the method wherein the operator sends a signal to the controller 60 to delivery fluid media M (e.g., saline solution or sterile water) through lumen 33 into chamber 30. FIG. 6 depicts the next step of the method wherein the controller delivers an intense discharge of electrical energy to the paired electrode elements 40A and 40B within chamber 30 indicated by electric arc or electric field EF. The electrical discharge provides energy exceeding the heat of vaporization of the contained fluid volume. The explosive vaporization of fluid media M (of FIG. 5) into a vapor or gas media is indicated at M' in FIG. 6. The greatly increased volume of gas media M' results in the gas being ejected from chamber 30 at high velocity through apertures 45 of surface 20A into the targeted tissue T. The liquid-to-vapor transition caused by the electrical discharge results in the vapor media M' having a temperature of 100° C. or more as well as carrying the heat of vaporization to deliver thermal effects into or through the targeted tissue T, as indicated graphically by the shaded regions of gas flow in FIG. 6. The fluid source and its pressure mechanism can provide any desired level of vapor ejection pressure. Depending on the character of the introduced liquid media, the media is altered from a first lesser temperature to a second greater temperature in the range of 100° C. or higher depending on pressure. The ejection of vapor media M' and its condensation will uniformly and very rapidly elevate the temperature of the engaged tissue to the desired range of about 65° C. to 100° C. to cause hydrothermal denaturation of proteins in the tissue, and to cause optimal fluid inter-mixing of tissue constituents that will result in an effective seal. In effect, the vapor-to-liquid phase transition of the ejected media M' will deposit heat equal to the heat of vaporization (also sometimes called the heat of condensation) in the tissue. At the same time, as the heat of vaporization of media M' is absorbed by water in the targeted tissue, the media converts back to a liquid thus hydrating the targeted tissue T. Such protein denaturation by hydrothermal effects differentiates this method of tissue sealing or fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is continuous or can be repeated at a high repetition rate to cause a pulsed form of thermal energy delivery in the engaged tissue. The fluid media M inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows for thermal relaxation of tissue, that may range from about 10 ms to 500 ms. The electrical source or voltage source 55 may provide a voltage ranging between about 20 volts and 10,000 volts to cause instant vaporization of the volume of fluid media M captured between the electrode elements 40A and 40B. After a selected time interval of such energy application to tissue T, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue T, the treated tissue will be fused or welded. Over time, the body's wound healing response will reconstitute the treated tissue by means of fibrosis to create a collagenous volume or scar-like tissue.

Figure 7:
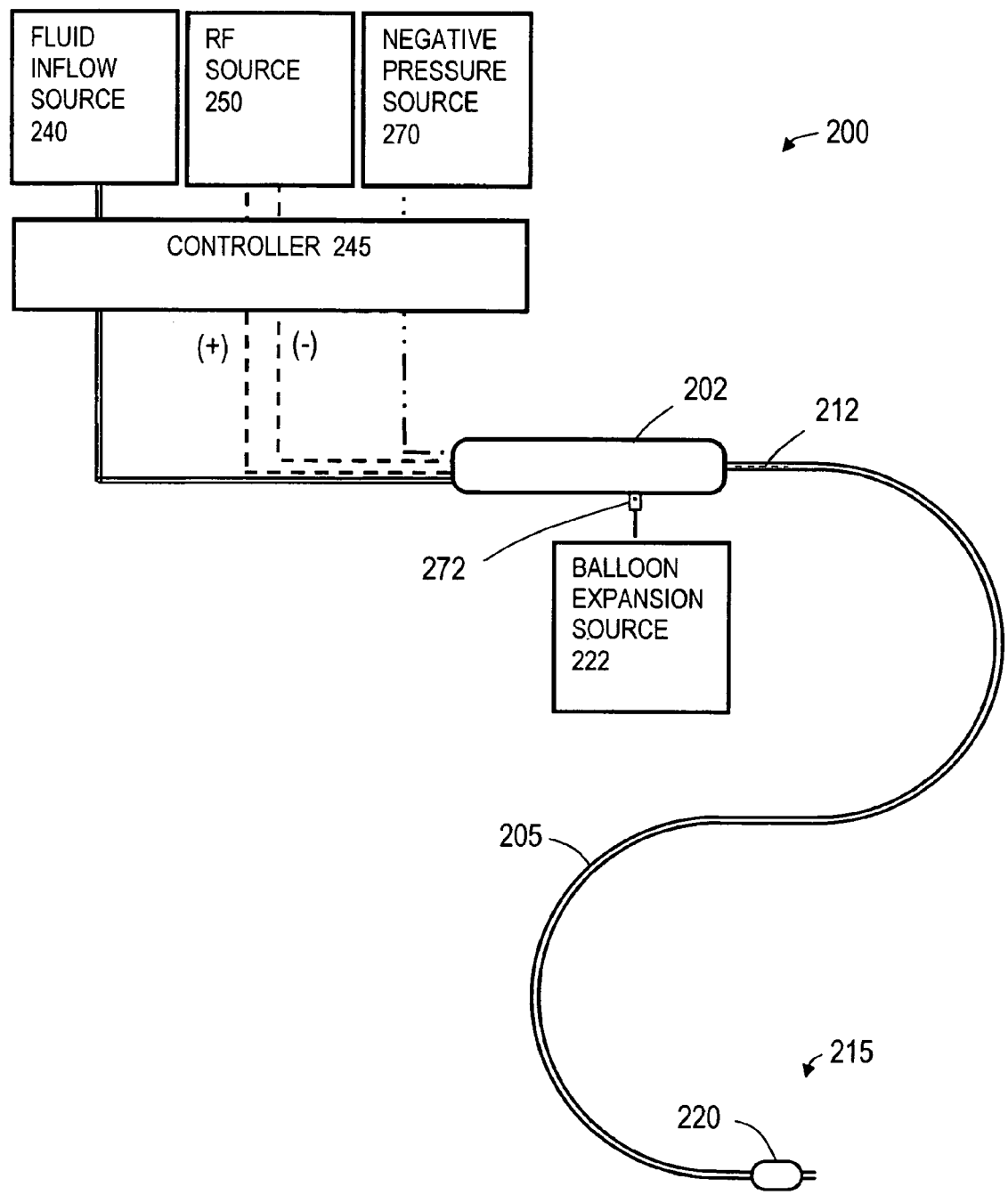
FIG. 7 a view of a Type "B" system of the invention with catheter working end configured for delivery of vapor to airway tissue to treat a lung disorder.
Figure 8:
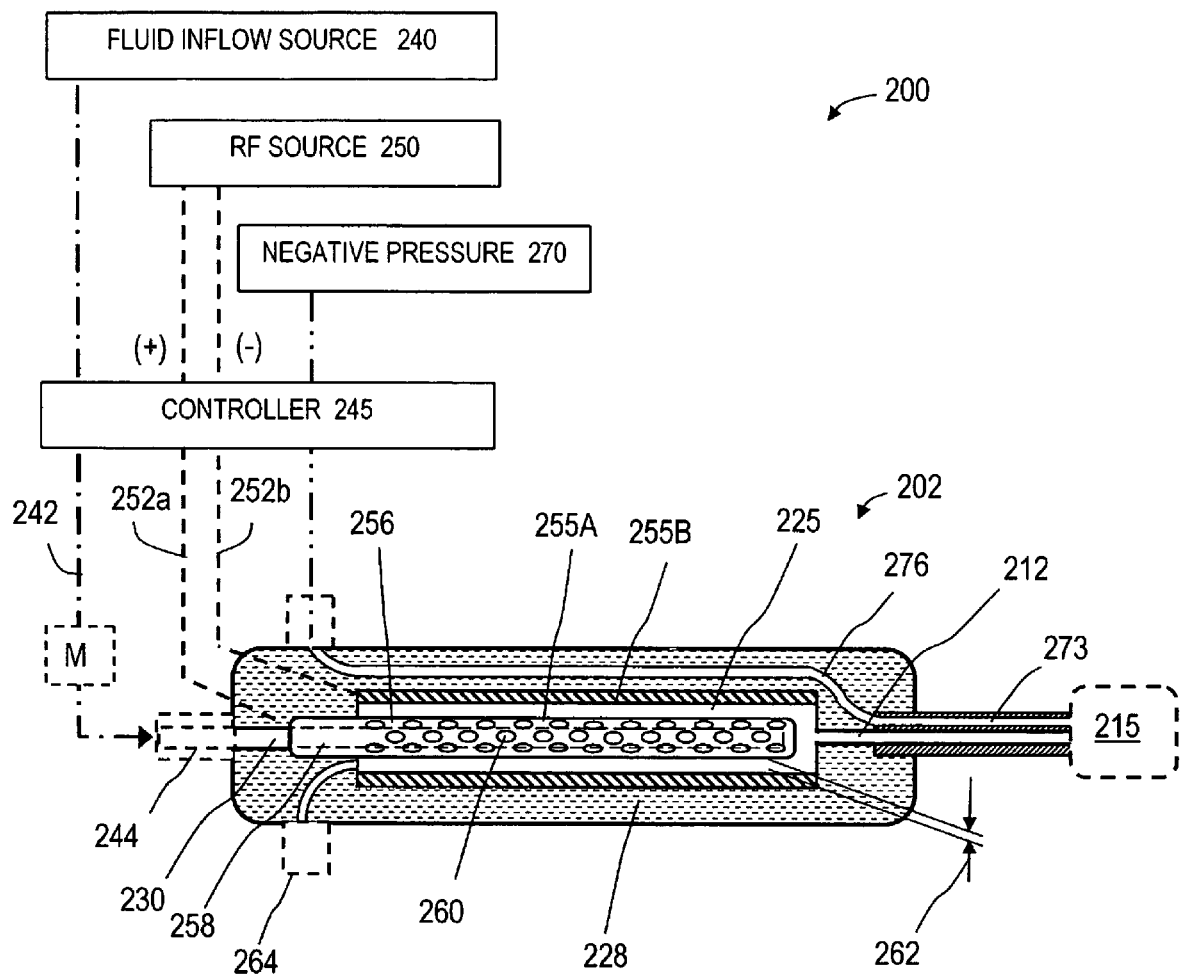
FIG. 8 is a cut-away view of the catheter handle of FIG. 7 depicting a thermal energy delivery mechanism for the liquid-to-vapor conversion of a pressurized inflow of a saline solution.

2. Type "B" Thermotherapy Instrument. Now referring to FIGS. 7 and 8, another embodiment of vapor generation and delivery system 200 is shown. In the previous embodiment, the working end was optimized for engaging and sealing tissue with a working surface that is in contact with tissue. In the embodiment of FIGS. 7 and 8, the working end is adapted for controlled application of energy by means of a vapor-to-liquid phase change energy release in an endoluminal application such as lung volume reduction or other treatments of airways.

In FIG. 7, it can be seen that system 200 includes a catheter handle portion 202 that transitions into an elongate catheter sleeve 205 that has an elongated dimension for introduction through a patient's airways, for example through the patient's oral or nasal cavities, to reach the lungs. The diameter of catheter sleeve 205 can range from about 2 Fr. to 6 Fr. or more. In a preferred embodiment, the catheter sleeve is configured for introduction through the working channel 208 of a bronchoscope indicated at 210 in FIG. 9. The catheter sleeve 205 also can be introduced in parallel with a bronchoscope, or a larger diameter catheter sleeve 205 can be provided a working channel to accommodate a scope.

Figure 9:
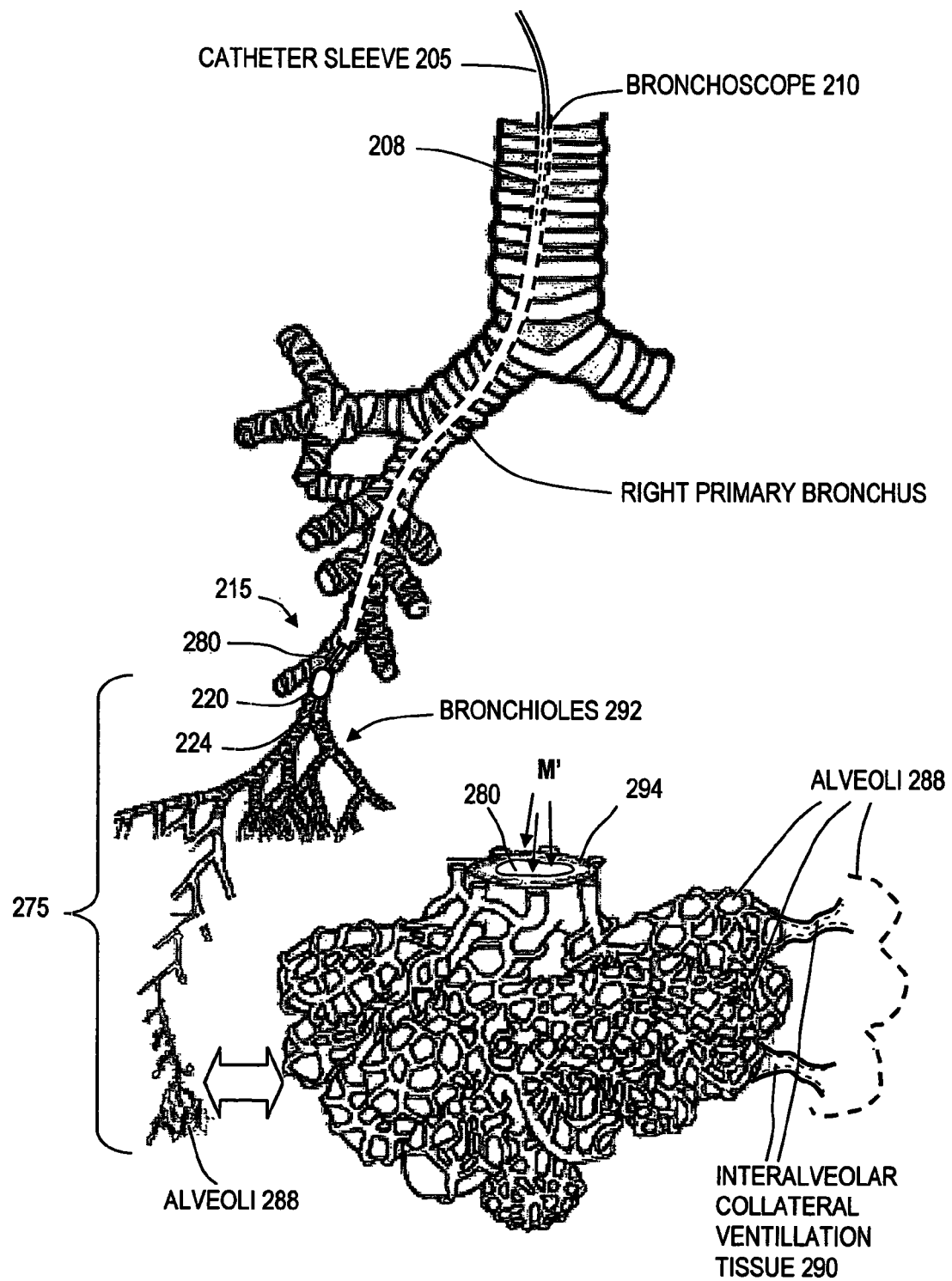
FIG. 9 is a schematic view of the use of the catheter of FIG. 7 in treating lung tissue for lung volume reduction.
Figure 10:
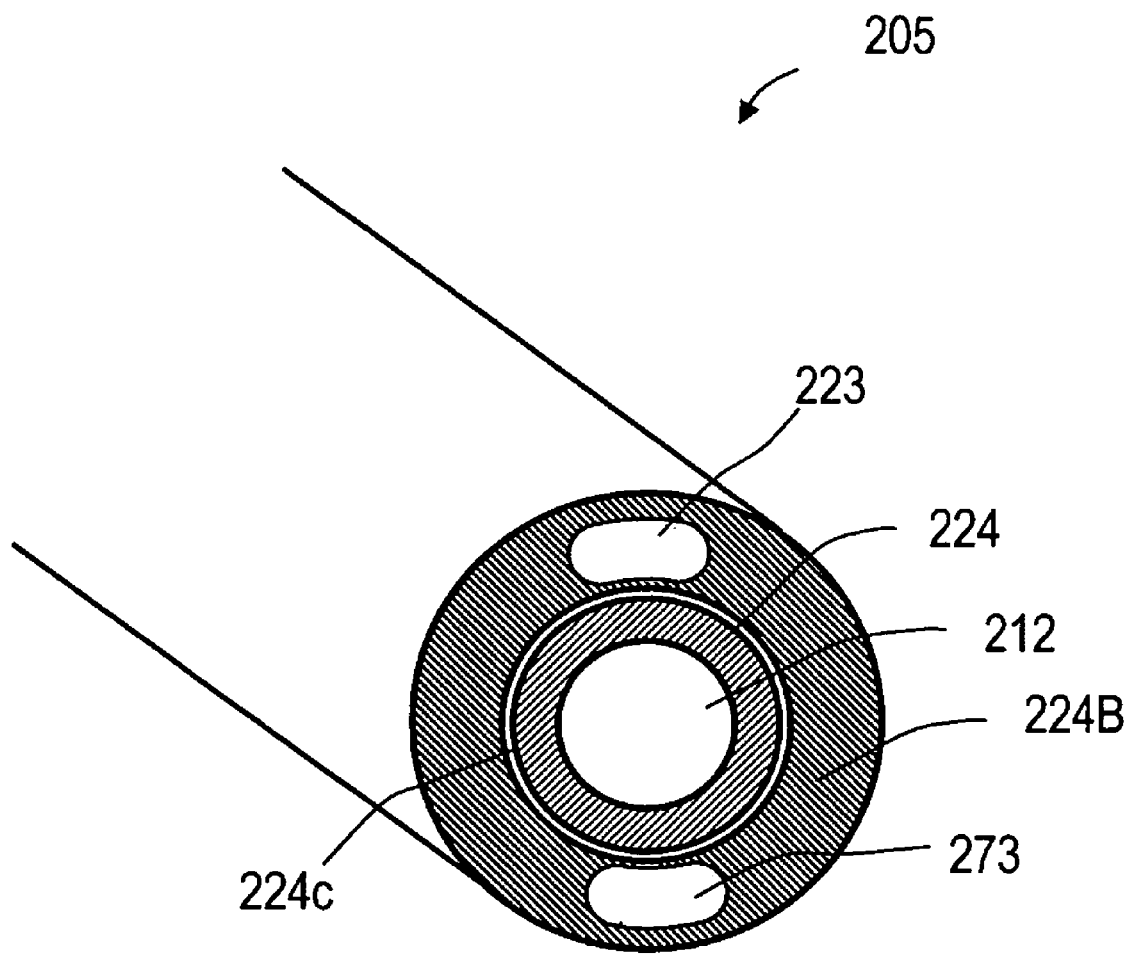
FIG. 10 is a sectional view of the catheter sleeve of FIG. 7.
Figure 11:
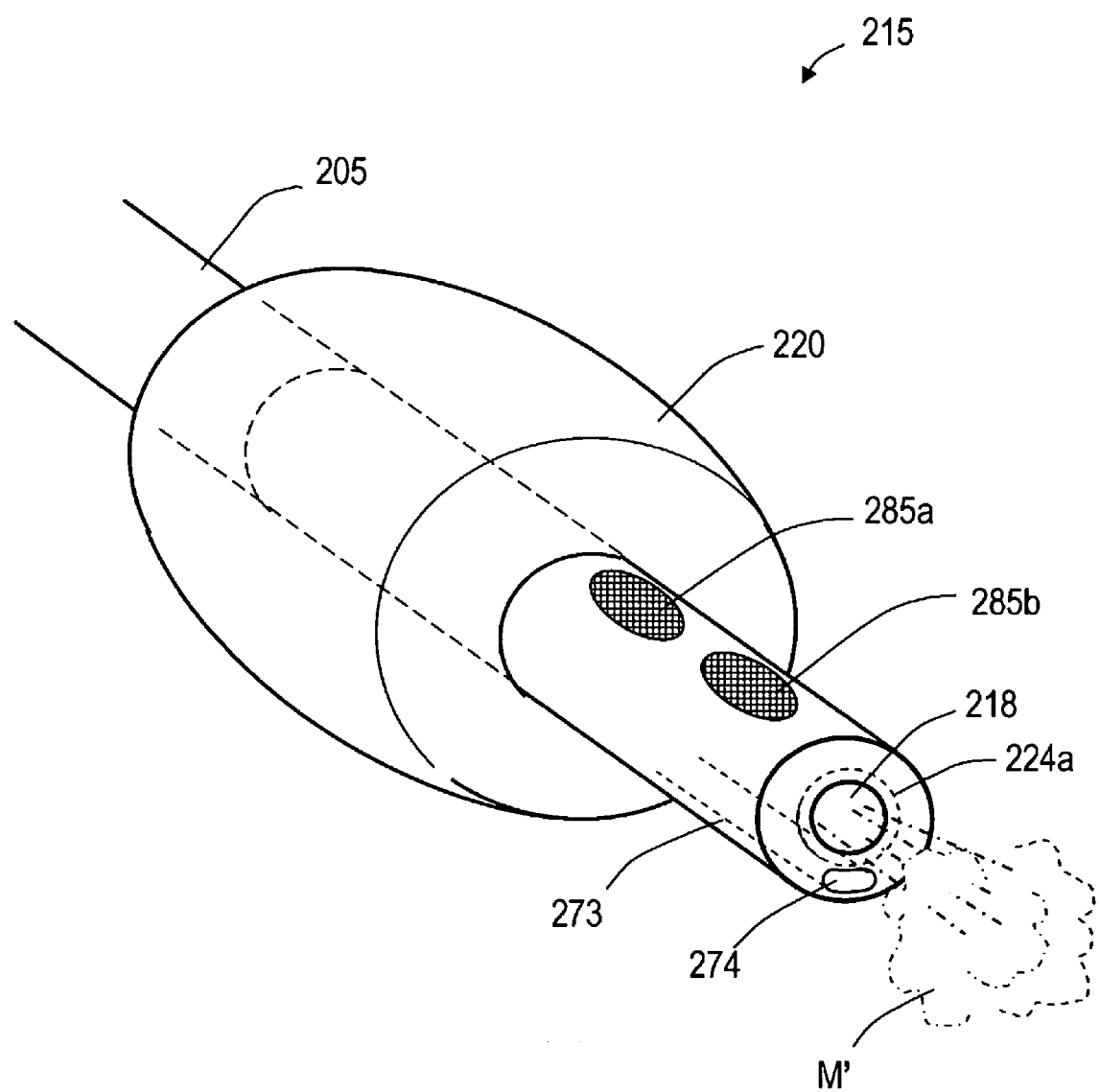
FIG. 11 is a perspective view of the working end of the catheter of FIG. 7.

The catheter sleeve 205 as shown in FIG. 7 has a outflow lumen or channel 212 extending from handle 202 for carrying vapor that is generated in the handle to working end 215 and the distal outlet 218 that is the termination of channel 212 (see FIG. 11). As can be seen in FIGS. 7, 9 and 11, the working end 215 carries a balloon 220 that can be expanded by means of inflation source 222 coupled to another lumen 223 in catheter sleeve 205 (see FIGS. 7 and 10). The balloon can be fabricated of any high temperature resistant polymer known in that art.

In preferred embodiments, the catheter sleeve 205 is fabricated of a single polymeric material or a combination of polymer layers 224a and 224b (FIG. 10). The exterior layer can have reinforcing in the form of braiding as is known in the art. In the embodiment of FIG. 10, the interior layer 224a is of a material having a low thermal conductivity, for example less than about 1.0 W/m-K, and preferably less than about 0.50 W/m-K. In one example, an unreinforced polyetheretherketone (PEEK) has a thermal conductivity of about 0.25 W/m-K and can be used for at least inner layer 224a of the catheter sleeve 205 (FIG. 10). PEEK is high temperature resistant engineered thermoplastic with excellent chemical and fatigue resistance plus thermal stability. PEEK had a maximum continuous working temperature of 480° F. and retains its mechanical properties up to 570° F. in high-pressure environments. Other materials used in the catheter can comprise formulations or blends of polymers that include, but are not limited to PTFE, polyethylene terephthalate (PET), or PEBAX. PTFE (polytetrafluoroethylene) is a fluoropolymer which has high thermal stability (up to 260° C.), is chemically inert, has a very low dielectric constant, a very low surface friction and is inherently flame retardant. A range of homo and co-fluoropolymers are commercialized under such names as Teflon®, Tefzel®, Neoflon®, Polyflon® and Hyflon®. In another embodiment, the catheter sleeve can carry another layer or structure 224c of any suitable thickness intermediate the inner and outer layers 224a and 224b that comprises a low thermal conductivity layer. Such a layer can comprise of air gaps, insulative ceramic or glass microspheres or fibers, or at least one lumen that carries a cryofluid in communication with a cryogenic fluid source as in known in the art (see FIG. 10).

Now turning to FIG. 8, the cut-away view of handle 202 shows that an interior chamber 225 is formed within the interior of an insulator material indicated at 228 such as a ceramic or a combination of materials to insulate the interior chamber 225 from the surface of the handle. An inflow channel 230 communicates with pressurized inflow source 240 of fluid or liquid media via flexible tube 242 coupled to fitting 244. A computer controller 245 is provided to control parameters of fluid inflows to the interior chamber 225. The interior chamber 225 has a distal region in which media flows transition to outflow channel 212 that extends to the working end 215. In FIG. 8, it can be seen that Rf source 250 (also operatively connected to controller 245) has first polarity (+) lead 252a and opposing second polarity (−) lead 252b that are coupled respectively to first and second conductive surfaces or electrodes 255A and 255B exposed in interior chamber 225 that serve as a thermal energy delivery mechanism. The first conductive surface 255A is the outer surface of elongated sleeve 256 with bore 258 therein having diffuser ports 260 in the sleeve wall for introducing pressurized liquid media M into the interior chamber 225. The diffuser ports 260 have a suitable dimension and configuration for diffusing or atomizing a high pressure inflow of flow media M from source 240, which preferably is a saline solution. The second polarity (−) lead is coupled to conductive surface 255B which comprises a radially outward surface of interior chamber 225. In the embodiment shown in FIG. 8, it can be seen that the first and second conductive surfaces 255A and 255B are concentric, extend over a substantial length of the handle and have a large surface area with a fixed spaced apart radial dimension indicated at 262. The radial dimension 262 between the electrode surfaces is selected to match the particular impedance and other operating characteristics of the Rf generator.

Referring to FIG. 8, in a method of operation, the system injects a volume liquid saline flow media M at a selected rate under pressure from source 240 which is diffused and atomized by ports 260 as the media enters interior chamber 225. Contemporaneous with injection and diffusion of the volume of saline, the system delivers sufficient current from source 250 and controller 245 to the conductive atomized saline via the opposing polarity surfaces 255A and 250B which instantly vaporize the $H_2O$ in the flow media M to generate a vapor M' that is injected from interior chamber 225 into lumen or channel 212 of catheter sleeve 205. The instantaneous increase in volume of media in the liquid-to-vapor phase transition greatly increases interior pressures in interior chamber 225 to thereby accelerate the flow into and through the catheter sleeve to working end 215. As shown in FIG. 8, the system and handle can include an optional pressure relief valve schematically indicated at 264 so that any overpressures in the interior chamber are released. The release of any overpressure can be vented through an additional lumen in the supply tube 242 or to another chamber in the handle.

As can be seen in FIGS. 7 and 9, the system further includes an inflation source 222 for inflating balloon 220. The balloon can be inflated with a gas or liquid from a syringe that can be attached to Luer fitting 272 that is in communication with lumen 223 in catheter sleeve 205 that extends to the inflation chamber of balloon 220.

Referring to FIGS. 8 and 9, the system further includes a negative pressure source 270 that communicates with another lumen 273 in catheter sleeve 205 that has an open distal termination 274 in a end portion of sleeve 205 distal to the expandable balloon (FIG. 11). The handle 202 further has a suitable channel indicated at 276 that extends between the negative pressure source 270 and aspiration lumen 273 in catheter sleeve. It should be appreciated that lumen 273 in catheter sleeve can also merge into the vapor delivery lumen 212 and still accomplish the method of the invention, it is preferred to have separate lumens that extend to the separate terminations in working end 215. As will be described below, lung volume reduction treatments benefit from application of suction or aspiration pressures that are controlled by controller 245.

FIG. 9 further depicts a method of the invention in treating a patient's lung for lung volume reduction. A bronchoscope 210 is shown with catheter sleeve 205 inserted through the working channel 208. The scope can be inserted through the patient's mouth or nasal passageway. The patient can be in an upright or supine position. Depending on whether the left or right lung is being treated, and whether the targeted lung portion is near the patient's heart, the patient's position may be adjusted to limit contact between the targeted lobe and the heart. In FIG. 9, it can be seen that the physician has navigated the working end 215 to the targeted region 275 of an airway 280 and actuated inflation source 222 to expand balloon 220 to occlude the airway. The deployment of balloon 220 is accomplished after viewing and selected the targeted airway region by means of the bronchoscope. The expanded balloon 220 will then direct all inflowing vapor in selected directions and toward the extremities of airway 280.

In a next step, based on a calculation of the volume of the bronchial tree 275 targeted for reduction, the physician sets the pressure, volume of vapor and rate of vapor delivery in the fluid inflow controller 245 that is operatively coupled to the fluid source 240, Rf source 250 and negative pressure source 270. The physician further selects the power level and duration of the Rf energy delivery at controller 245 to cooperate with the selected volume of inflowing media M. Next, the physician actuates the negative pressure or aspiration source 270 that communicates with lumen 273 in catheter sleeve 205 which extracts air from the targeted lung region 275 that is distal to occlusion balloon 220. The extraction of air can collapse the distal portion of the targeted lung region and better prepare the region for receiving the selected volume of vapor. The extraction of air can be accomplished over a selected aspiration interval ranging from about 10 seconds to 2 minutes or more. An optional pressure sensor 285*a* located at the distal end of the catheter 205 (FIG. 11) can be used to assist in determining when to terminate aspiration forces. MEMS-fabricated pressure sensors are known in the art and can be carried in the surface of the catheter or the balloon surface, for example, of the type fabricated by Integrated Sensing Systems, Inc., 391 Airport Industrial Drive, Ypsilanti, Mich. 48198. Such sensor can be linked back to controller 245 to adjust aspiration pressures or to trigger the next step of the method. The handle 202 can further carry an open-close valve (not shown) in the inflow lumen 212 that can be closed by controller 245 to prevent negative pressure from being applied to the interior chamber 225 or inflow supply tube 242.

The next step of the method of the invention includes termination of step of applying aspiration forces and causing controller 245 to contemporaneously actuate pressurized inflow source 240 and Rf source 250 to thereby inject liquid saline media M into interior chamber 225, cause a contemporaneous saline-to-vapor transition, and a contemporaneous pressurized injection of a volume of vapor media M' into targeted airway 280 (see FIG. 9). The pressure and duration of vapor delivery is sufficient to propagate the vapor media M' to the alveoli 288 in the targeted lung region. The inflow of vapor expands the targeted lung portion but at the same time the condensation of the vapor and its collapse in volume delivers energy without over-expanding the targeted bronchial tree region 275. In a preferred method and embodiment, the volume of the inflows decreases by at least about 500% upon collapse which releases the heat of vaporization. In more preferred methods and embodiments, the volume of the inflows decreases by at least about 1000% upon collapse and release of the heat of vaporization. The vapor delivers an amount of energy capable of modifying lung tissue by the shrinking and collapse of the treated lung tissue 275 to reduce lung volume. It has been found that the treated airways collapse instantly upon shrinkage of collagenous tissues in the airway walls which are not supported by substantial cartilage—which then results in fibrosis and permanent sealing of the treated airways. The permanent collapse of the airways will be immediate with fibrosis occurring over a period of several weeks. The method encompasses causing multiple desirable tissue modifications or effects for effective lung volume reduction including the shrinkage of lung tissue, the denaturation of lung tissue, the denaturation of collagen and proteins in airway walls, the damage, ablation or sealing of diseased or normal lung tissue, the occlusion of airways, the trigger of an immune response and the permanent remodeling of the targeted airways 275.

The method of the invention includes injecting the flow of vapor over a sufficiently short interval, for example less than about 30 seconds, to thereby substantially prevent conductive heat transfer to tissues external to the targeted airway. In other words, the heat of vaporization is deposited very quickly and the thermal relaxation time of the airway walls prevents substantial heating through the walls. In more preferred methods of practicing methods of the invention, the duration of energy delivery is less that about 15 seconds. By the methods described above, referring to FIG. 9, it has been found that shrinkage and related tissue modifications (described above) extends to alveoli 288 and interalveolar collateral ventilation tissue 290, as well as bronchioles 292, collagenous lung tissue 294, parenchyma and other lung tissue (whether diseased lung tissue or normal lung tissue).

The system and method of the invention preferably includes a pressure sensor 185*b* in the working end 215 that is coupled to controller 245 to sense excessive pressures in the targeted airways (see FIG. 11). The pressure sensor 185*b* can be set to open a valve, or to adjust an over-pressure valve 264 to automatically release pressure at any selected level. The sensor 185*b* can be of the type manufactured by Integrated Sensing Systems, Inc., 391 Airport Industrial Drive, Ypsilanti, Mich. 48198. The working end 215 can further carry a temperature sensor (not shown) that is coupled to controller 245 for modulating parameters of media inflows and energy delivery.

In a subsequent step of the method, the termination of the delivery of vapor media M' by controller 245 also contemporaneously actuates another step of the method wherein the negative pressure source 270 once again in turned on to extract air from just-treated bronchial tree region 275. The negative pressure source 270 aspirates condensed vapor from the airways and more importantly applies suction forces to the collapsed tissue as in relaxes thermally which assists in permanent remodeling of the tissue in the collapsed state. The method includes applying negative pressure to the targeted airways 275 for a selected interval programmed into controller 245 sufficient for tissue cooling and tissue remodeling, which can range from about 60 seconds to 10 minutes. Thereafter, the controller 245 terminates application of negative pressure to the treated airways 280. Upon a signal from the controller, the physician then deflates balloon 220 and withdraws the catheter from the patient to complete the procedure.

Figure 12:
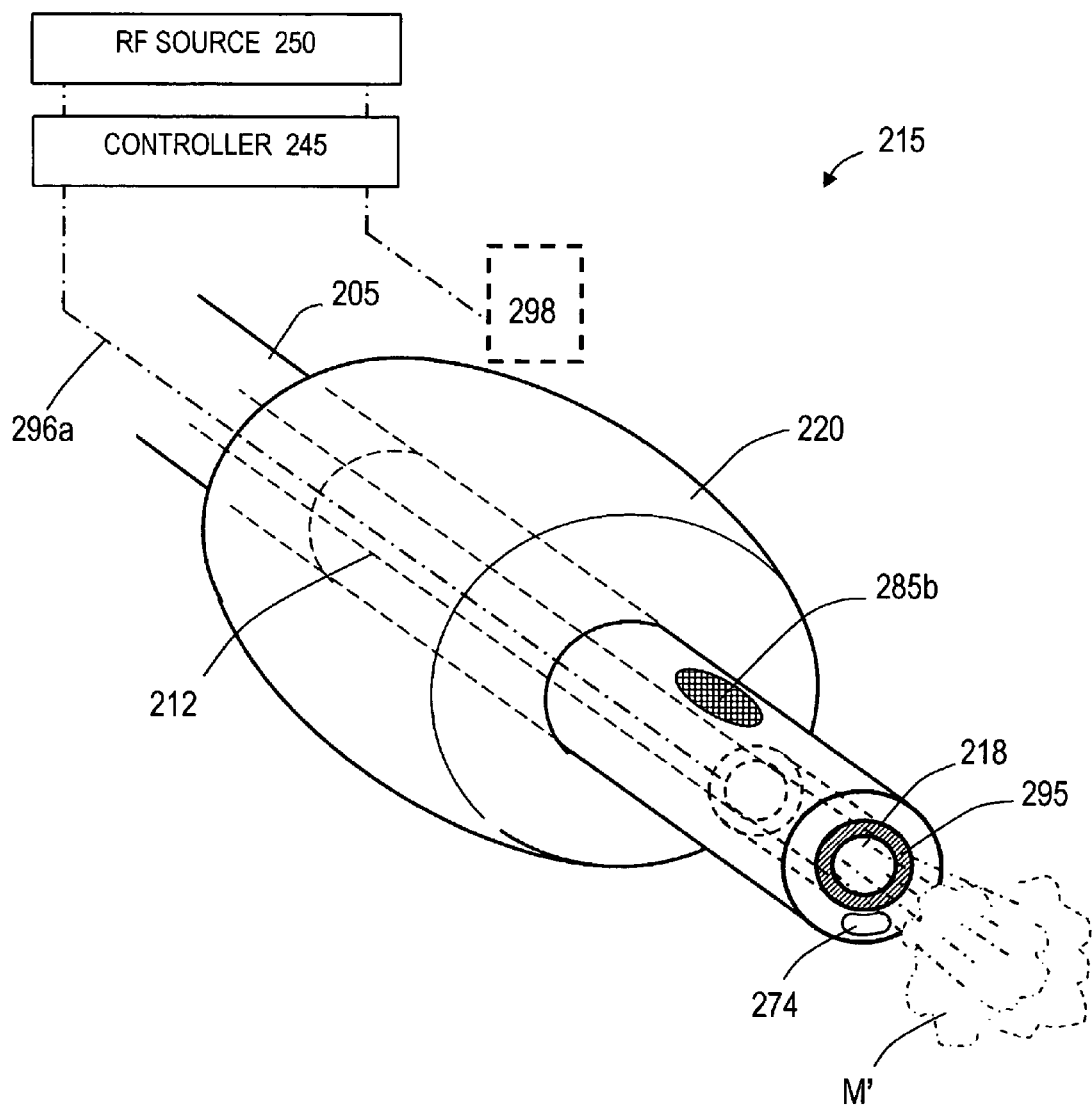
FIG. 12 is a perspective view of an alternative working end corresponding to the invention with at least one electrode for coupling electrical energy to vapor ejected from the working end.

In another preferred embodiment and method of the invention, referring to FIG. 12, the system 200 can include an optional electrode 295 exposed to the distal end of channel 212 in the catheter for coupling Rf energy to vapor M'. The Rf energy is provided from a suitable Rf source 250 that is coupled to electrode 295 by electrical lead 296a in the catheter wall. A second electrical lead 296b is connected to a ground pad 298 as is known in the art. In a method of use, the controller 245 actuates the Rf source contemporaneous with the flow of saline vapor M' from working end 215 wherein the conductive saline vapor can be energized and form a plasma for coupling energy to the surface of the targeted lung tissue 275. The system thus can couple electrical energy to the tissue in conjunction with the thermal effects of the vapor as described above. In this embodiment, it is preferred to use hypertonic saline solutions with high sodium chloride concentrations. The method of coupling Rf energy to saline vapor as it exits a medical device working end is further described in co-pending U.S. patent application Ser. No. 10/681,625, the entire contents of which are incorporated herein by this reference.

Figure 13:
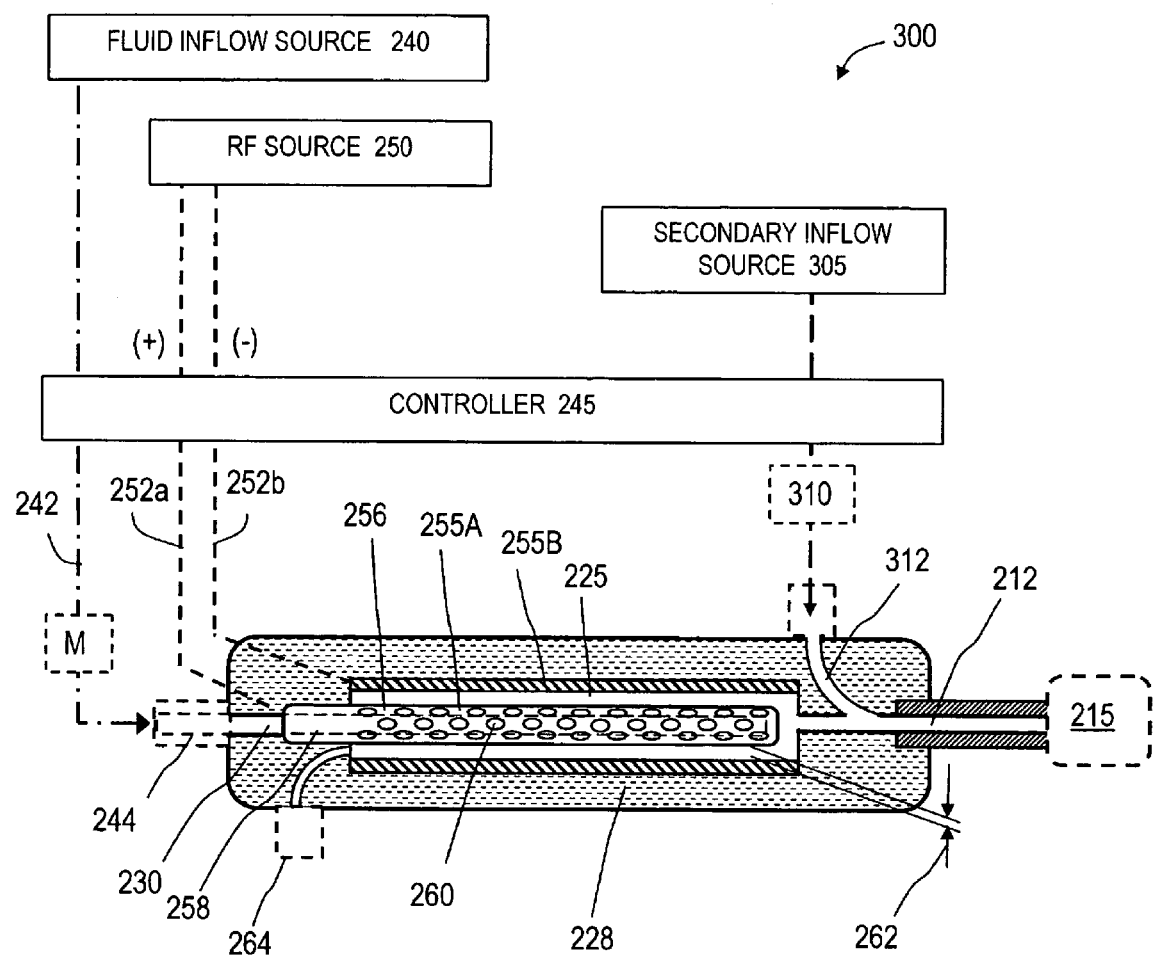
FIG. 13 is a cut-away view of an alternative catheter handle with a secondary source of an inflow media for reducing the mass average temperature of the ejected vapor.

In another embodiment and method of the invention, referring to FIG. 13, the system 300 can include a secondary pressurized media inflow source 305 that is adapted to introduce media or substance 310 (in the form of at least one of a gas, liquid or particulate) through channel 312 in the handle into channel 212 to combine with vapor media M' after it is ejected from chamber 225. In a method of the invention, the system thus allows for controlling the average mass temperature of the vapor. In one embodiment, the additional media 310 comprises a bioinert gas or atomized fluid that is depressurized and introduced into the vapor for the purpose of reducing the mass average temperature of the injected media to lower than about 100° C. For example, the introduced media 310 can be depressurized $CO_2$, $N_2$, or $O_2$ or atomized $H_2O$. By this means, the mass average temperature can be less than 100° C., for example in the range of about 45° C. to 100° C. More preferably, the mass average temperature can be in the range of about 60° C. to 95° C. Still more preferably, the mass average temperature can be in the range of about 70° C. to 90° C.

In another embodiment and method of the invention, still referring to FIG. 13, the system 300 can introduce additional media 310 that comprises a pharmacologically active substance with the vapor stream, such as any suitable anesthetic, to interact with lung tissue. In a similar embodiment and method of the invention, the system 300 can introduce additional media or substance 310 that enhances ablation or damage of the targeted tissue such as any sclerosing agent. The substance 310 also can be ethyl alcohol which will enhance damage to the tissue targeted for treatment. The substance 310 also can be any toxin, e.g., Botulinum Toxin Type A, that can enhance local tissue damage for lung volume reduction. The substance 310 also can be Tetracycline or another antibiotic that damages endothelial tissues to promote a strong immune response resulting in strong adhesions and collagen formation.

In another embodiment, the system of FIG. 13 can introduce a gas or substance that comprises an imaging enhancement media as known in the art. The method of the invention further includes the step of imaging the flow of vapor as it propagates distally in the targeted airway 280 (FIG. 9). The system can use hyperpolarized noble gases, for example as known in the field of using hyperpolarized $^3$Helium-magnetic resonance imaging ($^3$He-MRI) to assess the pathophysiology of ventilation and perfusion in patients with lung disease.

Figure 14:
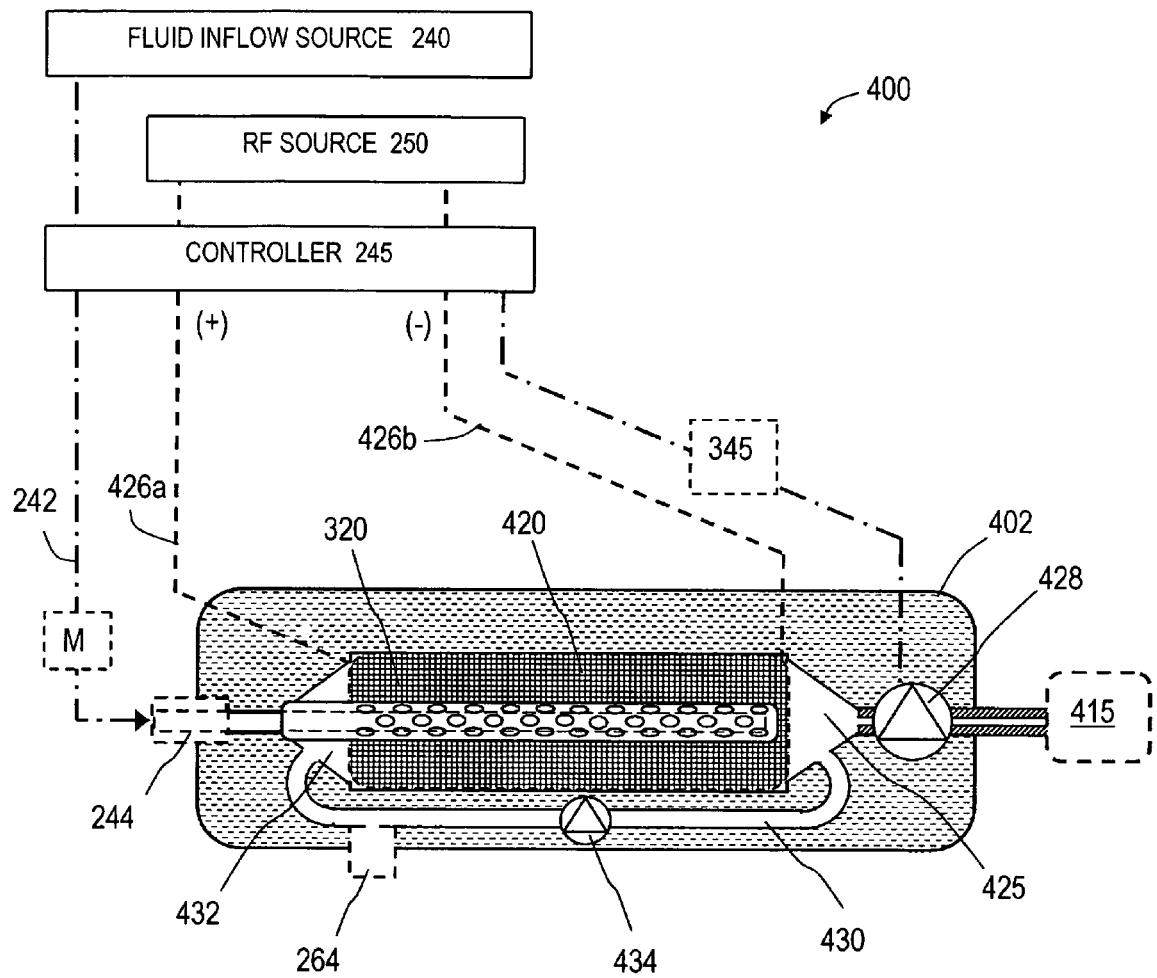
FIG. 14 is a cut-away view of an alternative catheter handle that utilizes a resistive heating structure together with a recirculation channel causing the liquid-to-vapor conversion of a pressurized inflow of a selected inflow media.

FIG. 14 illustrates another system embodiment 400 with handle 402 that utilizes a resistive element 420 in interior chamber 425 to cause the liquid-to-vapor phase change in the inflowing media M. All other system components are similar to the previous embodiments and have similar reference numbers. The electrical leads 426a and 426b in this embodiment are coupled to opposing ends of resistive element 420. In one embodiment, the resistive element 420 comprises a flow permeable structure such as a syntactic material or open-cell material (FIG. 14). The terms "syntactic", "open-cell" and "flow permeable" as used herein refer to any structure that has substantial porosity for allowing fluid flow therethrough. Such materials have the advantage of providing very high surface areas for conducting heat from an $I^2R$ heated material to pressurized media flows therein. The syntactic structure is further selected to provide an internal pore dimension that causes diffusion and atomization of high pressure inflows, for example of sterile water or saline. For example, the resistive element 420 can comprise a syntactic metal, resistive ceramic composite, or include a carbon portion. Such materials are available from ERG Materials and Aerospace Corp., 900 Stanford Avenue, Oakland, Calif. 94608 and Poco Graphite (http://www.poco.com). The open-cell material also can be an open cell foam that is metal plated, a sintered material, a plated entangled filament material, or any ordered or disordered structure commonly known in the art.

In the embodiment of FIG. 14, the system further includes a valve system 428 and recirculating channel 430 that are adapted for controlling the generation and release of vapor from working end 415. In the previous embodiments, the use of Rf energy delivery for vapor generation in chamber 225 (FIG. 8) can cause instantaneous high pressure flows of vapor. In the system embodiment of FIG. 13, the delivery of energy by means of resistive element 420 can require a fraction of a second or more to produce vapor from high pressure inflows of liquid media M. For this reason, the interior chamber 425 includes a recirculation channel 430 for a looped flow of vapor—or vapor and water droplets—that circulates back to inflow channel or the proximal end 432 of interior chamber 425. It should be appreciated that the recirculation channel 430 can be entirely housed in handle 402 or can circulate back to the source 245 or another intermediate chamber. The recirculation channel 430 also is operatively coupled to a pressure relief valve 262 as described above, and can further include a one-way valve indicated at 434. In operation of the embodiment, the system is actuated to create vapor which can circulate until a switch 435 coupled to controller 245 and valve 428 is actuated to release vapor M' from interior chamber 425. In all other respects, the method of the invention is the same as described above.

The schematic view of system 400 in FIG. 14 depicts the valve 428 in the handle, but the valve can also be located in working end 415 or elsewhere in catheter sleeve 205. Such valve systems can be linked to controller 245 by electrical leads in the catheter wall. In another embodiment, the valve 428 can be in the working end 415 and the recirculation channel 430 also can extend through the catheter sleeve 205 to the working end 415. This system thus assures that high quality vapor will be ejected from the working end.

The scope of the invention includes the use valve system 428 and recirculating channel 430 in other embodiments that utilize Rf, laser microwave or other energy deliver mechanisms. For example, in an Rf energy system as in FIG. 8, the valve and recirculating channel 430 systems can be used to control slight inconsistencies in vapor generation due to varied liquid inflow rates that sometimes results in sputtering and incomplete vaporization or inflowing media.

In another embodiment, still referring to FIG. 14, a system that utilizes a resistive element 420 for vapor generation also well suited for a method of the invention that introduces an alternative media or a combination media M into interior chamber 425 that has another lower or high heat of vaporization. By this means, the method of the invention includes controlling the temperature of the heat of vaporization which in turn controls the release of energy for ablating tissue. In one embodiment, for example, the system can vaporize alcohol which will lower the amount of energy delivered per unit volume of vapor as well as enhance the thermal ablation.

In another embodiment similar to that of FIG. 14, the system can use a "compression-decompression" system for generating a therapeutic vapor. In such a system, an external high pressure source infuses heated water (or saline or another liquid) from the external source into an enclosed interior chamber of the system. The system also includes a valve similar to valve 428 in FIG. 14. Upon opening of the valve, the release of pressurized fluid will in part release the energy that was exerted on the fluid in the form of pressure—which will be converted into the energy required to vaporize the heated fluid. This type of system has the advantage of not requiring a thermal energy source with sufficient capacity for vaporizing needed volumes of vapor. Instead, a pressurization mechanism combined with a less robust thermal energy delivery system can be used to produce the required volume of vapor. Such a source would typically be external to the handle of the catheter.

In another method of the invention, a catheter system can be used for cryotherapy of the lung, wherein thermal cooling or freezing methods known in the art could promote lung volume reduction via the wound healing response to such cryotherapy. In one embodiment, a high pressure liquid nitrogen source external to the catheter comprises a source for cold nitrogen gas. The handle of the catheter includes a valve for releasing the cryofluid which would expand the targeted lung region. Introduction of such nitrogen gas from the working end 215 of the catheter would result in instantaneous freezing of surface tissues of the targeted airway 275 (cf. FIG. 9). Due to the nature of ice crystal formation in tissue, the affected cells would burst due to a physical expansion in size. The damaged lung tissue would then remodel as it progresses through the normal wound healing response. The treated airway also could be blocked with a plug to help prevent the airway from expanding until fibrosis has occurred over a period of several weeks. Other liquids also can be used in a cryotherapy, such as oxygen and carbon dioxide.

Although the invention is described to treating a patient's lung for lung volume reduction, the scope of the invention includes applying energy to lung tissue for other disorders such as asthma and the like.

The invention as described in detail above utilizes Rf energy delivery means or a resistive heating means. The scope of the invention includes applying energy from other suitable sources such as coherent of broadband light energy, microwave, ultrasound or magnetic inductive heating of liquid media to generate suitable vapor as are known to those skilled in the art.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of treating a disorder of a lung comprising:
generating a flow of vapor;
introducing the flow of vapor into a targeted airway of the lung at a pressure sufficient to extend the flow of vapor to extremities of the targeted airway;
delivering thermal energy to the lung tissue via a vapor-to-liquid phase transition of the vapor; and
modifying the lung tissue to treat the disorder.

2. The method of claim 1 further comprising generating the flow of vapor by at least one of resistive heating means, radiofrequency (Rf) energy means, microwave energy means, photonic energy means, magnetic induction energy means, compression and decompression means, and ultrasonic energy means.

3. The method of claim 1, further comprising controlling at least one of the pressure of the flow of vapor, the volume of the flow of vapor and the duration of the flow of vapor.

4. The method of claim 1, further comprising controlling the temperature of the heat of vaporization of the vapor.

5. The method of claim 1 wherein modifying lung tissue includes at least one of shrinkage, denaturation, damage, ablation, sealing, occlusion, an immune response or remodeling of lung tissue.

6. The method of claim 5 wherein the lung tissue includes at least one of bronchi, bronchioles, alveoli, parenchyma, diseased lung tissue, normal lung tissue, collagenous lung tissue and interalveolar collateral ventilation tissue.

7. The method of claim 1 wherein introducing the flow of vapor includes introducing the flow over a sufficiently short interval to substantially prevent conductive heat transfer to body structure external to a targeted airway.

8. The method of claim 1 including generating the vapor from at least one of water, saline and alcohol.

9. The method of claim 1 wherein introducing the flow of vapor includes introducing at least one substance with the vapor.

10. The method of claim 9 wherein the substance is an imaging enhancing media.

11. The method of claim 1 including introducing at least one pharmacologically active agent with the vapor.

12. The method of claim 11 wherein the pharmacologically active agent is at least on one of an anesthetic, an antibiotic, a toxin and a sclerosing agent.

13. The method of claim 1 further comprising imaging the flow of vapor.

14. The method of claim 1 wherein introducing the flow of vapor is preceded by expanding an expansion structure in a proximal portion of a targeted airway for controlling the direction of the flow of vapor.

15. The method of claim 14 wherein expanding the expansion structure includes evacuating air from the airway distal to the expansion structure.

16. The method of claim 1 further comprising the step of applying negative pressure to the targeted airway after terminating the flow of vapor.

17. The method of claim 16 wherein applying negative pressure is performed for an interval sufficient for at least one of tissue cooling and tissue remodeling.

18. The method of claim 1 wherein the heat of vaporization of the vapor is above about 45' C.

19. The method of claim 1 further comprising coupling electrical energy to the flow of vapor.

20. The method of claim 1 wherein the disorder of the lung comprises emphysema.

21. The method of claim 1 further comprising expanding an occlusion balloon in a proximal portion of the targeted airway to direct the flow of vapor toward the extremities of the targeted airway.

22. A method of treating a disorder of a lung comprising:
generating a flow of vapor;
expanding an expansion structure in a proximal portion of a targeted airway to occlude the airway;
introducing the flow of vapor into the lung distal to the expansion structure;
delivering thermal energy to the lung tissue via a vapor-to-liquid phase transition of the vapor; and
modifying the lung tissue to treat the disorder.

23. The method of claim 22 wherein the expansion structure directs the flow of vapor toward extremities of the targeted airway.

24. The method of claim 22 wherein introducing the flow of vapor includes introducing the flow over a sufficiently short interval to substantially prevent, conductive heat transfer to body structure external to a targeted airway.

25. The method of claim 22 wherein modifying lung tissue includes at least one of shrinkage, denaturation, damage, ablation, sealing, occlusion, an immune response or remodeling of lung tissue.

26. The method of claim 22 wherein the disorder of the lung comprises emphysema.

27. The method of claim 22 wherein the lung tissue includes at least one of bronchi, bronchioles, alveoli, parenchyma, diseased lung tissue, normal lung tissue, collagenous lung tissue and interalveolar collateral ventilation tissue.

* * * * *